Figure 1:
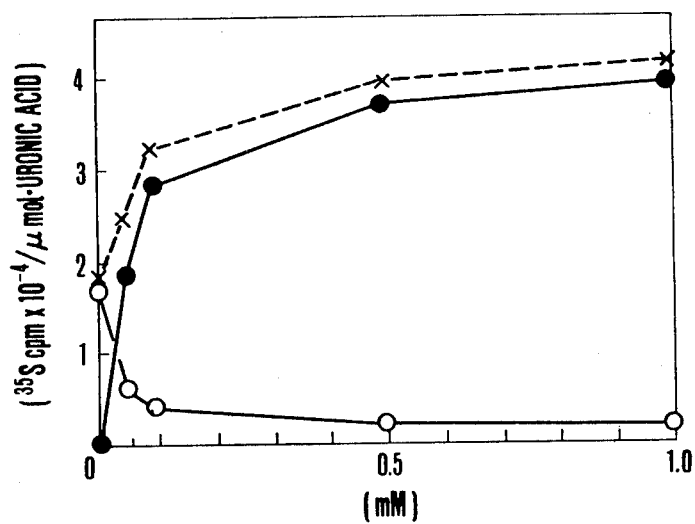

United States Patent [19]

Noyori et al.

[11] 4,454,123
[45] Jun. 12, 1984

[54] O-XYLOPYRANOSIDE SERIES COMPOUNDS AND METHODS OF USE

[75] Inventors: Ryoji Noyori, Aichi; Sakaru Suzuki; Minoru Okayama, both of Nagoya; Katukiyo Sakurai, Takahagi; Shigeyoshi Kamohara, Akigawa; Yoshio Ueno, Kodaira, all of Japan

[73] Assignee: Seikagaku Kogyo Co. Ltd., Tokyo, Japan

[21] Appl. No.: 472,786

[22] Filed: Mar. 7, 1983

Related U.S. Application Data

[63] Continuation-in-part of Ser. No. 326,502, Dec. 2, 1981, abandoned.

[30] Foreign Application Priority Data

Dec. 9, 1980 [JP] Japan .................... 55-172625
May 1, 1981 [JP] Japan .................... 56-65226
May 1, 1981 [JP] Japan .................... 56-65227
Sep. 14, 1981 [JP] Japan .................... 56-144001
Nov. 4, 1981 [JP] Japan .................... 56-175772

[51] Int. Cl.$^3$ .................... C07H 15/18; C07H 15/04; C07H 5/06; A61K 31/70
[52] U.S. Cl. .................... 424/180; 536/1.1; 536/4.1; 536/22
[58] Field of Search .................... 536/1.1, 4.1, 22; 424/180

[56] References Cited

U.S. PATENT DOCUMENTS 3,940,383 2/1976 Fujiwara et al. .................... 536/4.1
4,315,921 2/1982 Yoshikumi et al. .................... 536/22

OTHER PUBLICATIONS

Sivakumaran et al., "Chem. Abst.", vol. 67, 1967, p. 11713(t).
Kersters–Hilderson et al., "Chem. Abst.", vol. 72, 1970, p. 96923(p).
Deleyn et al., "Chem. Abst.", vol. 92, 1980, p. 193427(a).

Primary Examiner—Johnnie R. Brown
Attorney, Agent, or Firm—Frishauf, Holtz, Goodman & Woodward

[57] ABSTRACT

Disclosed is a D-xylopyranoside series compound represented by the following general formula:

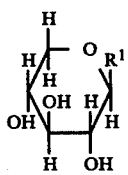

in which $R^1$ represents a benzyl group,

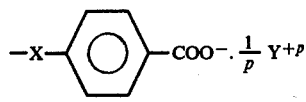

(X, Y and p are as defined in the specification),

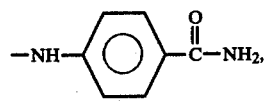

—S—$R^2$ ($R^2$ is as defined in the specification), or an alkyl group having from 6 to 25 carbon atoms, said compounds alter the nature and amount of proteoglycan on the surface of tumor cells to thereby enhance the immune reaction to said tumor cells.

6 Claims, 9 Drawing Figures

O-XYLOPYRANOSIDE SERIES COMPOUNDS AND METHODS OF USE

This application is a continuation-in-part application of the parent application U.S. Ser. No. 326,502 filed on Dec. 2, 1981, now abandoned.

This invention relates to novel D-xylopyranoside series compounds, and more particularly to D-xylopyranoside series compounds which have the properties to change nature and quantity of the glycoconjugate(proteoglycan) existing on the surface of cell membranes and which are thus expected to bring effects to inhibit a transplantable cancer such as Sarcoma-180, vascular sclerosis, thrombus and the like.

It has heretofore been known that O-$\beta$-D-xylopyranoside series compounds change quantity of the so-called proteoglycan, which exists at the surface of cell membranes or between cells and which is one of important components constituting organism tissues, and they also greatly alter the properties of the surfaces of a certain type of cell membranes [J. Biochem. 74, 1069–1073 (1973)].

For example, with respect to tumor cells, the O-$\beta$-D-xylopyranoside series compounds can change the properties of proteoglycan on the surface of the tumor cells and reduce the quantity thereof so as to strip the tumor cells naked, so to speak. Thus, it is well expected that the O-$\beta$-D-xylopyranoside series compounds will enhance the immunity of the living organisms to the tumor cells in order to prevent an attack of tumors and to thereby improve therapeutic effects.

When utilized as therapeutic medicines, however, these compounds have to fulfill requirements such as a low toxicity, allowance of a long-term administration, a harmless teratogenecity and allergic reaction, a high safety and the like.

As substances of satisfying such requirements, there are mentioned D-xylopyranoside series compounds having paracarboxyphenyl groups as aglycons.

Heretofore, as the above-mentioned D-xylopyranoside series compound having the paracarboxyphenyl group as the aglycon, N-paracarboxyphenyl-D-xylopyranosyl amine has been reported (Nougei Kagaku Zasshi (Agricultural Chemistry Magazine), 25, 61, 1950).

This N-paracarboxyphenyl-D-xylopyranosyl amine can be expected to show the effects of altering the properties of the proteoglycan and decreasing its necessary amount, similarly to the above-mentioned O-$\beta$-D-xylopyranoside series compounds. In order to obtain such effects, however, a relatively large amount thereof will disadvantageously be required.

In other words, the above-mentioned conventional O-$\beta$-D-xylopyranoside series compounds are liable to be hydrolyzed by enzymes. For example, when such a compound is administered to a human body for the purpose of inhibiting a tumor, the major portion of the administered compound is decomposed to a useless form before showing its effects.

The inventors have found out D-xylopyranoside series compounds which hardly tend to be hydrolyzed by virtue of enzymes and which can nevertheless maintain the property to alter in a minor amount the nature and the quantity of the proteoglycan existing on the surfaces of cells, and completed the present invention.

An object of the present invention is to provide novel types of D-xylopyranoside compound.

Namely, the present invention provides D-xylopyranoside a series compound represented by the following general formula (1):

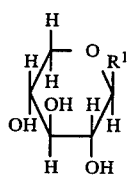

(1)

in which $R^1$ represents a benzyl group,

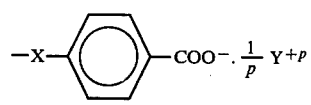

(X represents an oxygen, a sulfur or a methylene group; Y represents a hydrogen, a lithium, a sodium, a potassium, a magnesium, a calcium or an aluminum atom; and p represents a valency of an atom represented by Y),

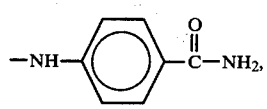

—S—$R^2$ ($R^2$ represents a straight-chain alkyl group having from 7 to 25 carbon atoms or a branched alkyl group having from 3 to 25 carbon atoms, a straight-chain or a branched alkenyl group having from 3 to 25 carbon atoms, or a straight-chain or a branched alkynyl group having from 3 to 25 carbon atoms), or an alkyl group having from 6 to 25 carbon atoms.

It is preferred that a monovalent hydrocarbon group represented by the above-mentioned $R^2$ is a straight-chain alkyl group having from 7 to 18 carbon atoms or a branched alkyl group having from 3 to 18 carbon atoms, an alkenyl group having from 3 to 18 carbon atoms, or an alkynyl group having from 3 to 18 carbon atoms, because a D-xylopyranoside series compound represented by the general formula (1) containing such a hydrocarbon group have noticeable effect as an initiator for the biosynthesis of chondroitin sulfate.

The alkyl group represented by $R^1$ includes n-hexyl, n-neptyl, n-octyl, n-nonyl, n-decyl, n-undecyl, n-dodecyl (n-lauryl), n-tridecyl, n-tetradecyl (n-myristyl), n-pentadecyl, n-hexadecyl (n-cetyl), n-heptadecyl, n-octadecyl (n-stearyl), n-nonadecyl, n-eicosyl, n-henicosyl, n-docosyl, n-tricosyl, n-tetracosyl and n-pentacosyl, which pertain to a straight-chain alkyl group, but the group $R^1$ may be a branched alkyl group.

The D-xylopyranoside series compounds according to the present invention are novel, as the specific compounds represented by the above-mentioned formula (1), there may be exemplified the following compounds.

(1) C-Benzyl-$\beta$-D-xylopyranoside
(2) Paracarboxyphenyl-$\delta$-D-xylopyranoside
(3) Paracarboxyphenyl 1-thio-$\beta$-D-xylopyranoside
(4) C-Paracarboxybenzyl-$\beta$-D-xylopyranoside [4-(C-$\beta$-D-xylopyranosyl)methyl-1-benzoic acid]
(5) Para(lithiumoxycarbonyl)phenyl-$\beta$-D-xylopyranoside
(6) Para(lithiumoxycarbonyl)phenyl 1-thio-$\beta$-D-xylopyranoside (7) C-Para(lithiumoxycarbonyl)benzyl-β-D-xylopyranoside [lithium 4-(C-β-D-xylopyranosyl)-methyl-1-benzoate]
(8) Para(sodiumoxycarbonyl)phenyl-β-D-xylopyranoside
(9) Para(sodiumoxycarbonyl)phenyl 1-thio-β-D-xylopyranoside
(10) C-Para(sodiumoxycarbonyl)benzyl-β-D-xylopyranoside [sodium 4-(C-β-D-xylopyranosyl)-methyl-1-benzoate]
(11) Para(potassiumoxycarbonyl)phenyl-β-D-xylopyranoside
(12) Para(potassiumoxycarbonyl)phenyl 1-thio-β-D-xylopyranoside
(13) C-Para(potassiumoxycarbonyl)benzyl-β-D-xylopyranoside [potassium 4-(C-β-D-xylopyranosyl)-methyl-1-benzoate]
(14) Para(magnesiumoxycarbonyl)phenyl-β-D-xylopyranoside
(15) Para(magnesiumoxycarbonyl)phenyl 1-thio-β-D-xylopyranoside
(16) C-Para(magnesiumoxycarbonyl)benzyl-β-D-xylopyranoside [magnesium 4-(C-β-D-xylopyranosyl)methyl-1-benzoate]
(17) Para(calciumoxycarbonyl)phenyl-β-D-xylopyranoside
(18) Para(calciumoxycarbonyl)phenyl 1-thio-β-D-xylopyranoside
(19) C-Para(calciumoxycarbonyl)benzyl-β-D-xylopyranoside [calcium 4-(C-β-D-xylopyranosyl)-methyl-1-benzoate]
(20) Para(aluminiumoxycarbonyl)phenyl-β-D-xylopyranoside
(21) Para(aluminiumoxycarbonyl)phenyl 1-thio-β-D-xylopyranoside
(22) C-Para(aluminiumoxycarbonyl)benzyl-β-D-xylopyranoside [aluminium 4-(C-β-D-xylopyranosyl)methyl-1-benzoate]
(23) N-Paracarbamoylphenyl-D-xylopyranosylamine
(24) n-Heptyl 1-thio-β-D-xylopyranoside
(25) n-Octyl 1-thio-β-D-xylopyranoside
(26) n-Nonyl 1-thio-β-D-xylopyranoside
(27) n-Decyl 1-thio-β-D-xylopyranoside
(28) n-Undecyl 1-thio-β-D-xylopyranoside
(29) n-Lauryl 1-thio-β-D-xylopyranoside
(30) n-Tridecyl 1-thio-β-D-xylopyranoside
(31) n-Myristyl 1-thio-β-D-xylopyranoside
(32) n-Pentadecyl 1-thio-β-D-xylopyranoside
(33) n-Cetyl 1-thio-β-D-xylopyranoside
(34) n-Heptadecyl 1-thio-β-D-xylopyranoside
(35) n-Stearyl 1-thio-β-D-xylopyranoside
(36) n-Eicosyl 1-thio-β-D-xylopyranoside
(37) n-Docosyl 1-thio-β-D-xylopyranoside
(38) n-Tetracosyl 1-thio-β-D-xylopyranoside
(39) Isopropyl 1-thio-β-D-xylopyranoside
(40) Isobutyl 1-thio-β-D-xylopyranoside
(41) sec-Butyl 1-thio-β-D-xylopyranoside
(42) Isoamyl 1-thio-β-D-xylopyranoside
(43) Neopentyl 1-thio-β-D-xylopyranoside
(44) sec-Isoamyl 1-thio-β-D-xylopyranoside
(45) Isohexyl 1-thio-β-D-xylopyranoside
(46) Isononyl 1-thio-β-D-xylopyranoside
(47) Isolauryl 1-thio-β-D-xylopyranoside
(48) Isopentadecyl 1-thio-β-D-xylopyranoside
(49) Isostearyl 1-thio-β-D-xylopyranoside
(50) Allyl 1-thio-β-D-xylopyranoside
(51) Propargyl 1-thio-β-D-xylopyranoside
(52) C-n-Hexyl-β-D-xylopyranoside (C-β-D-Xylopyranosylhexane)
(53) C-n-Heptyl-β-D-xylopyranoside (C-β-D-Xylopyranosylheptane)
(54) C-n-Octyl-β-D-xylopyranoside (C-β-D-Xylopyranosyloctane)
(55) C-n-Nonyl-β-D-xylopyranoside (C-β-D-Xylopyranosylnonane)
(56) C-n-Decyl-β-D-xylopyranoside (C-β-D-Xylopyranosyldecane)
(57) C-n-Undecyl-β-D-xylopyranoside (C-β-D-Xylopyranosylundecane)
(58) C-n-Lauryl-β-D-xylopyranoside (C-β-D-Xylopyranosyldodecane)
(59) C-n-Tridecyl-β-D-xylopyranoside (C-β-D-Xylopyranosyltridecane)
(60) C-n-Myristyl-β-D-xylopyranoside (C-β-D-Xylopyranosyltetradecane)
(61) C-n-Pentadecyl-β-D-xylopyranoside (C-β-D-Xylopyranosylpentadecane)
(62) C-n-Cetyl-β-D-xylopyranoside (C-β-D-Xylopyranosylhexadecane)
(63) C-n-Heptadecyl-β-D-xylopyranoside (C-β-D-Xylopyranosylheptadecane)
(64) C-n-Stearyl-β-D-xylopyranoside (C-β-D-Xylopyranosyloctadecane)
(65) C-n-Nonadecyl-β-D-xylopyranoside (C-β-D-Xylopyranosylnonadecane)
(66) C-n-Eicosyl-β-D-xylopyranoside (C-β-D-Xylopyranosyleicosane)
(67) C-n-Henicosyl-β-D-xylopyranoside (C-β-D-Xylopyranosylhenicosane)
(68) C-n-Docosyl-β-D-xylopyranoside (C-β-D-Xylopyranosyldocosane)
(69) C-n-Tricosyl-β-D-xylopyranoside (C-β-D-Xylopyranosyltricosane)
(70) C-n-Tetracosyl-β-D-xylopyranoside (C-β-D-Xylopyranosyltetracosane)
(71) C-n-Pentacosyl-β-D-xylopyranoside (C-β-D-Xylopyranosylpentacosane).

The C-benzyl-β-D-xylopranoside in which $R^1$ in the general formula (1) is a benzyl group may be synthesized in accordance with the following reaction route:

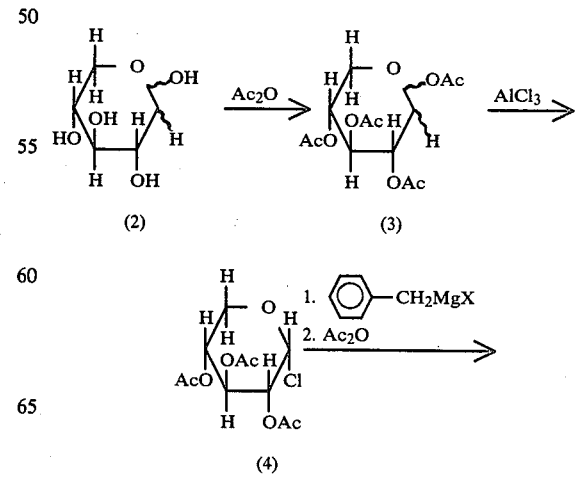

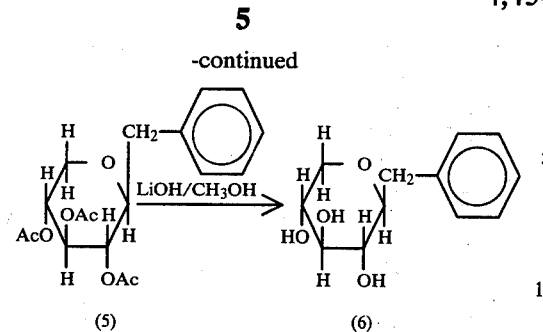

(in the above reaction route and formulae, Ac represents an acetyl group ($CH_3CO$) and X represents a halogen atom such as bromine).

That is, D-xylose (2) is acetylated to form a tetraacetate (3) by the method proposed by Hudson et al. [C. S. Hudson, J. M. Johnson, J. Am. Chem. Soc., 37, 2748 (1915)]. The tetraacetate (3) thus obtained is then treated with aluminum chloride to give a compound (4) by the method proposed by Holland et al. [C. V. Holland, D. Horton, J. S. Jewell, J. Org. Chem., 32, 1818 (1967)]. At this stage, the β-form of compound (4) is obtained when the tetraacetate (3) is treated with aluminum chloride for a short period of time; the α-form of compound (4), which is thermodynamically stable, is obtained when the time of the treatment with aluminum chloride is longer. The compound (4) can be prepared also by treating the D-xylose (2) with acetyl chloride in the presence of zinc chloride [J. Am. Chem. Soc., 37, 2748 (1915) mentioned above].

Thereafter, the obtained compound (4) is treated with an excess of Grignard reagent, followed by acetylation to give a compound (5). At this stage, both α- and β-forms of the compound (5) are formed. The β-form thereof can be separated from the α-form by means of chromatography, recrystallization or the like. The thus obtained β-form of the compound (5) is then treated in methyl alcohol with a catalytic amount of a base such as lithium hydroxide or sodium hydroxide to yield the desired compound in which the group $R^1$ of the general formula (1) is a benzyl group, according to the present invention.

A compound of the present invention in which the group $R^1$ in the general formula (1) is

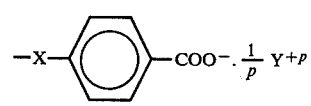

may be synthesized in accordance with the following reaction route. Namely, in the case of a compound where the group X in the formula (1) is oxygen, the route is as follows:

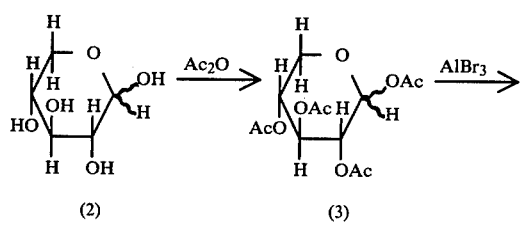

That is, the above-mentioned compound (7) may be obtained in the same manner as in the previous preparation of the compound in which the group $R^1$ is a benzyl group, except that aluminum chloride, zinc chloride and acetyl chloride are replaced with aluminum bromide, zinc bromide and acetyl bromide.

The obtained compound (7) is then reacted with parahydroxymethyl benzoate in the presence of silver oxide to obtain a compound (8). The thus obtained β-form compound (8) is treated with a catalytic amount of a base such as lithium hydroxide or sodium hydroxide in methanol to produce a desired compound (9) of the present invention.

Next, a compound in which the group X in the formula (1) is sulfur may be prepared in accordance with the following reaction route, where the same formulae as in the reaction route for preparing the compound having an oxygen group as X are represented by the same numbers.

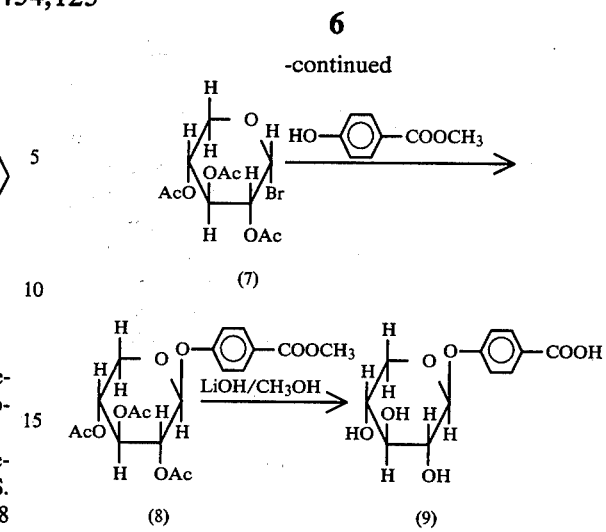

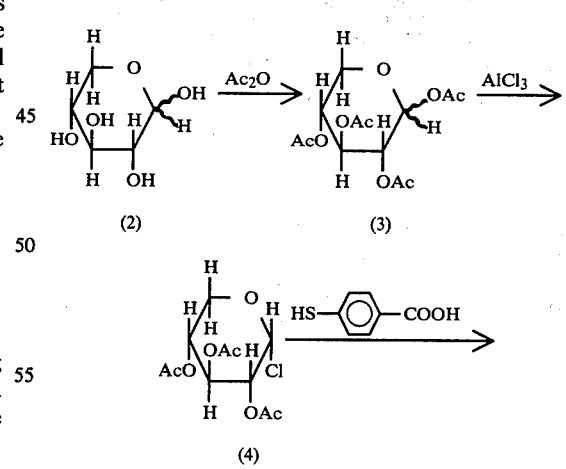

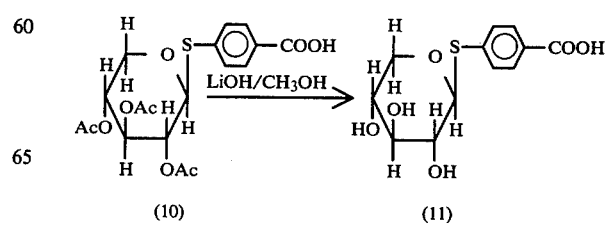

Namely, the compound (4) may be obtained from the same materials and route as in the preparation of the compound having oxygen as the above-mentioned X, except that the compound (3) is treated with aluminum chloride in place of aluminum bromide. The obtained compound (4) is allowed to react with paramercaptobenzoic acid or its sodium salt to prepare a compound (10). The thus obtained β-form compound (10) is treated with a catalytic amount of a base such as lithium hydroxide or sodium hydroxide in methanol to prepare a desired compound (11) in which the group $R^1$ in the general formula (1) is

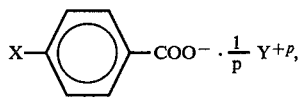

according to the present invention.

Further, a compound in which the group X in the formula (1) is methylene group may be prepared in accordance with the following reaction route, where the same formulae as in the reaction route for preparing the compound having sulfur as the X are represented by the same numbers.

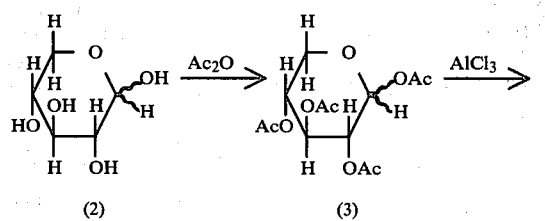

(2)          (3)

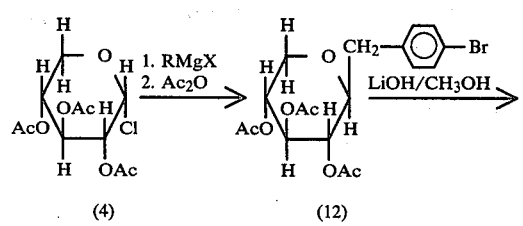

(4)          (12)

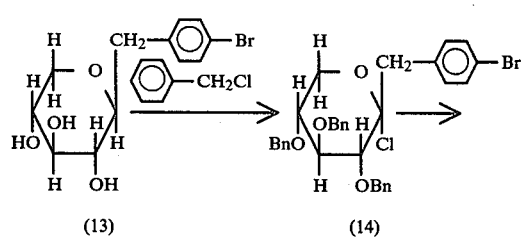

(13)          (14)

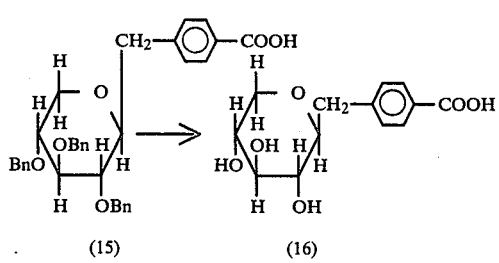

(15)          (16)

(in the above-mentioned formulae and reaction route, X denotes a parabromobenzyl group Bn represents a benzyl group, and Ac is as defined above).

Namely, in accordance with the same route as in the case where the above-mentioned X is sulfur, the compound (4) may be obtained. Then, after the treatment of the compound (4) with the aid of an excess Grignard reagent, it may be subjected to acetylation to produce a compound (12). At this time, the compound thus produced contains α- and β-forms. The separation between the α-form and β-form can be carried out by utilizing a suitable manner such as chromatography, recrystallization or the like. The thus obtained β-form compound (12) is treated with a catalytic amount of a base such as lithium hydroxide or sodium hydroxide in methanol to yield a compound (13).

Thereafter, the compound (13) is reacted with an excess benzyl chloride to yield tri-O-benzyl compound (14), which is then allowed to react with carbon dioxide gas for the purpose of introducing a carboxyl group thereto in order to yield a compound (15). The thus obtained compound (15) is reacted with a catalytic amount of palladium-carbon to yield the desired compound (16).

Furthermore, in the case where the group Y in the formula (1) is a metallic atom instead of hydrogen, these compounds (9), (11) and (16) which can be obtained through the above-mentioned reaction routes are each dissolved in an alcohol-water system solvent, followed by mixing with an inorganic salt of a required metal for substitution, to yield a desired compound of a metallic salt.

A compound of the present invention in which the group $R^1$ in the formula (1) is

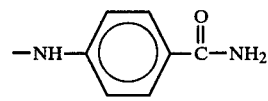

may be prepared by reacting D-xylose with p-aminobenzamide in the presence of an acid.

A compound of the present invention in which the group $R^1$ in the formula (1) is $-S-R^2$ may be synthesized in accordance with the following reaction route.

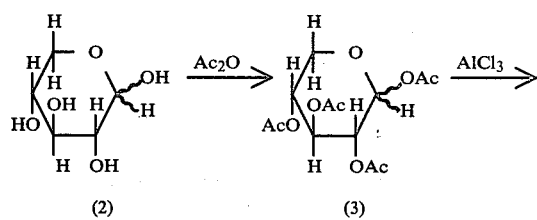

(2)          (3)

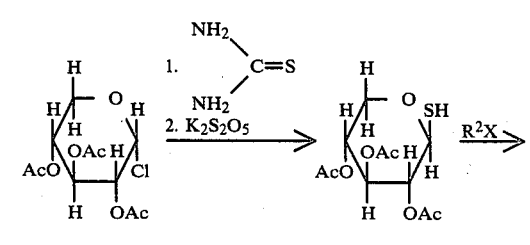

(4)          (17)

-continued

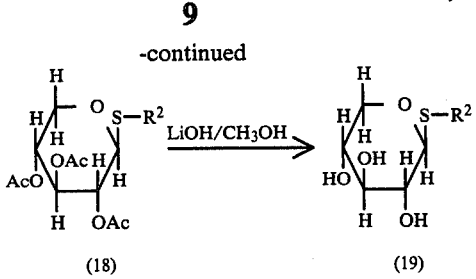

(in the above-mentioned formulae and reaction route, X represents bromine or iodine, and Ac and R are as defined above).

That is, a compound (4) is synthesized in the same manner as in mentioned above.

The obtained compound (4) is then reacted with thiourea and subsequently potassium pyrosulfate to yield a compound (17), which is further allowed to react with bromide or iodide represented by $R^2X$ to yiled a compound (18). The thus obtained compound (18) is treated with a catalytic amount of a base such as lithium hydroxide in metanol to yield the desired compound (19) in which $R^1$ in the formula (1) is $-S-R^2$.

A compound of the present invention in which the group $R^1$ in the general formula (1) is an alkyl group having from 6 to 25 carbon atoms may be synthesized in accordance with the following reaction route:

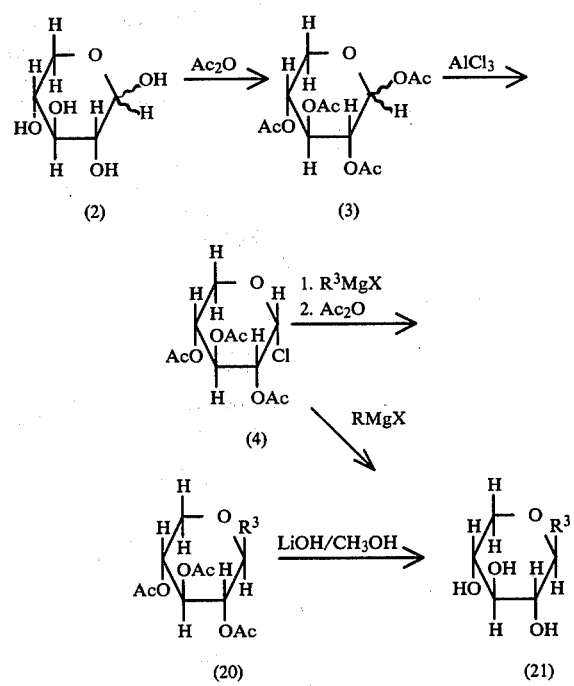

(in the above-mentioned formulae and reaction route, Ac is as defined above, X represents a halogen atom such as a bromine atom, and $R^3$ represents an alkyl group having from 6 to 25 carbon atoms).

That is, a compound (4) is synthesized in the same manner as in mentioned above.

The thus obtained compound (4) is then treated with an excess Grignard reagent to yield a desired compound (21) of the present invention. Alternatively, after the compound (4) has been treated with an excess Grignard reagent, followed by acetylation, the resultant compound is refined for isolation of β-form compound, which is then treated with a catalytic amount of a base such as lithium hydroxide or sodium hydroxide to yield the desired compound (21) of the present invention.

The thus prepared D-xylopyranoside series compounds of the present invention can serve as a satisfactory initiator for the biosynthesis of chondroitin sulfate, as shown below in Test Examples 1 to 5 and FIGS. 2 and 3. In addition, the glycosaminoglycan synthesized by using the D-xylopyranoside series compounds of the present invention as the initiator combines with no protein components and has an extremely lower molecular weight (molecular weight: $2.0 \times 10^4$ to $3.0 \times 10^4$) as compared with normal proteoglycan (molecular weight: $2.5 \times 10^6$ or more), hence it is hard for the glycosaminoglycan to remain in tissues. Therefore, the glycosaminoglycan in a tissue culture system will be liberated into the culture medium, and in an animal body, it will be liberated from tissues into the blood stream. Thus, when the D-xylopyranoside compound of the present invention is administered to a living organism, the proteoglycan on the surface of the cell membranes constituting the tissues will decrease in quantity and the low molecular weight glycosaminoglycan (e.g., chondroitin sulfate) formed under the action of the D-xylopyranoside compounds of the present invention as an initiator will conclusively be liberated into the blood stream. Explanation of this effect can be given employing transplantable cancer cells such as Sarcoma-180 as an example: the compound of the present invention causes the quantity of the proteoglycan on the transplantable cancer cell (Sarcoma-180) surfaces to considerably reduce, so that the cancer cells become, so to speak, a stripping state, and the immunity of the living organisms to a transplantable cancer is enhanced by the immune cells. Accordingly, it is well expected that the compounds of the present invention will be useful for prevention and therapy of transplantable cancers (such as Sarcoma-180).

Further, the glycosaminoglycan (e.g., chondroitin sulfate) liberated into the blood stream has the same effects on a living organism as the chondroitin sulfate which is specially administered to the living organism from the exterior. Thus, it is expected that the compounds of the present invention will be effective for the prevention and therapy of various diseases caused by the lipid deposition onto the walls of blood vessels and the vascular sclerosis. In addition, the D-xylopyranoside series compounds of the present invention are less vulnerable to the hydrolysis by acids and enzymes, as compared with conventional O-β-D-xylopyranoside compounds. Thus, the compounds of the present invention involve no possibility of suffering from decomposition before they reach the so-called target organs. Further, it has been found that the D-xylopyranoside series compounds have an influence on the synthesis of the glycosaminoglycan (chondroitin sulfate) at a 1/5 to ½ lower concentration than conventional N-paracarboxyphenyl-D-xylopyranosylamine and thereby serve as a good initiator for the synthesis of the chondroitin sulfate. This is a valuable advantage over the conventional D-xylopyranoside compounds.

Furthermore, the compound according to this invention shows an effect of inhibition of platelet agglutination caused by several kinds of platelet agglutinating agents such as ADP, collagen, thrombin, ristocetin and epinephrine. It can therefore be expected that the compound according to this invention may be useful as a pharmaceutical for the therapy of thrombosis.

Figure 2:
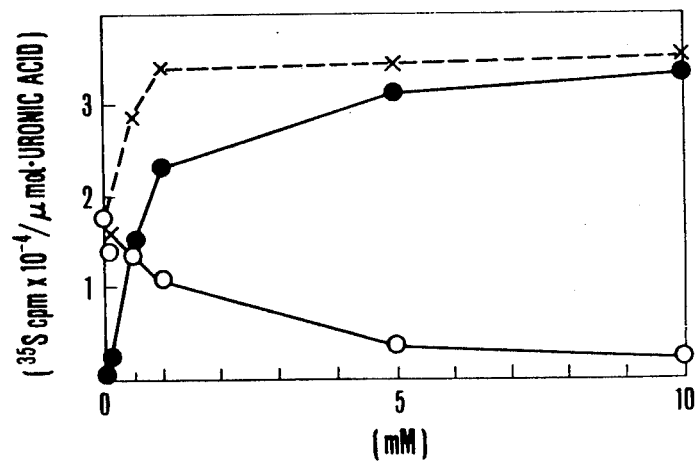

The present invention will be explained taking Examples and Test Examples in accordance with accompanying drawings:

FIGS. 1 and 2 are graphs showing influence of O-paranitrophenyl-β-D-xylopyranoside and C-benzyl-β-D-xylopyranoside (a compound of the present invention), respectively, on the synthesis of chondroitin sulfate;

FIGS. 3 to 7 are graphs showing influence of O-paranitrophenyl-β-xylopyranoside, N-para(sodiumoxycarbonyl)phenyl-D-xylopyranosylamine, para(sodiumoxycarbonyl)phenyl-β-D-xylopyranoside (a compound of the present invention), C-para(sodiumoxycarbonyl)benzyl-β-D-xylopyranoside (a compound of the present invention), and para(sodiumoxycarboxyl)phenyl 1-thio-β-D-xylopyranoside (a compound of the present invention), respectively, on the synthesis of chondroitin sulfate.

Figure 8:
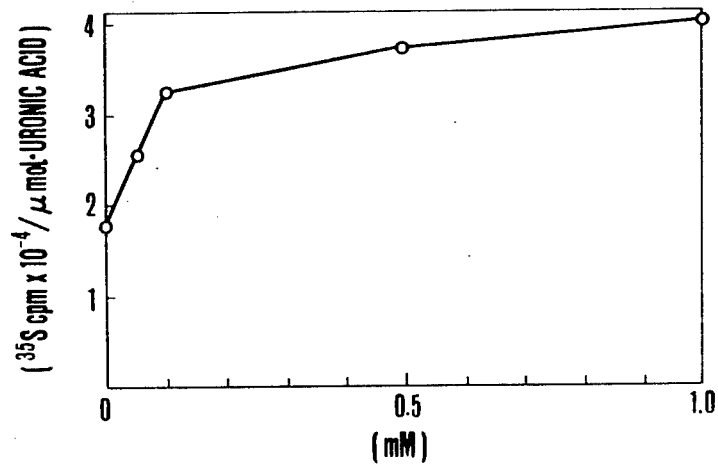
Figure 9:
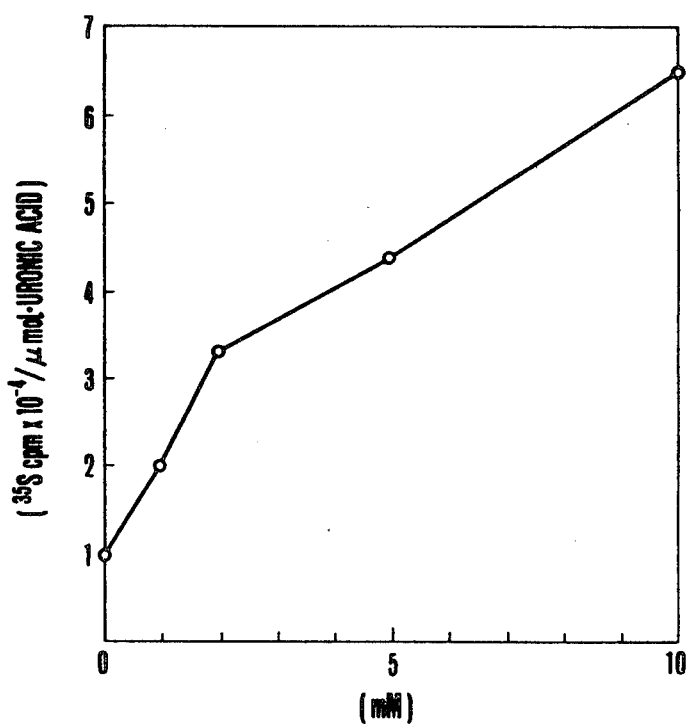

FIGS. 8 and 9 are graphs showing influence of O-paranitrophenyl-β-D-xylopyranoside (a conventional compound) and N-paracarbamoylphenyl-D-xylopyranosylamine (a compound of the present invention) on the synthesis of chondroitin sulfate.

EXAMPLE 1

Synthesis of C-benzyl-β-D-xylopyranoside

To an ethereal solution (500 ml.) containing excess benzylmagnesium chloride, there was added dropwise an ethereal solution (500 ml.) containing 50 g. of tri-O-acetyl-α-D-xylosyl chloride (4) over 30 minutes. After completion of the dropwise addition, the resulting reaction mixture was refluxed for 2 hours. After cooled to room temperature, the reaction mixture was poured gradually into one liter of an ice-water. The mixture was acidified with acetic acid and then an organic layer was separated. The resulting aqueous layer was concentrated under reduced pressure, followed by vacuum drying to obtain a white solid. After finely crushed, the solid was put into a two-liter eggplant type flask. To the flask, 60 g. of anhydrous sodium acetate and 700 ml. of acetic anhydride were added, and then the resulting reaction mixture was stirred at 100° C. for two hours. After completion of the stirring operation, the acetic anhydride was distilled away under reduced pressure, and extraction based on ethyl acetate, rinsing and drying were in turn carried out to obtain a syrup. The thus obtained syrup was subjected to silica gel column chromatography to yield 22 g. of tri-O-acetyl-C-benzyl-β-D-xylopyranoside (5).

To mixture of 22 g. of the prepared tri-O-actyl-C-benzyl-β-D-xylopyranoside, 100 mg. of lithium hydroxide and 100 ml. of a dried methanol was stirred at room temperature for one hour. After the reaction mixture was concentrated under reduced pressure, the resulting residue was subjected to silica gel column chromatography to yield 10 g. of C-benzyl-β-D-xylopyranoside (C-β-D-xylopyranosylmethylbenzene). The yield was 30%.

$[\alpha]_D^{20} = -56.3°$ (c=1, H$_2$O).
IR(cm$^{-1}$): 3430, 1600 cm$^{-1}$.
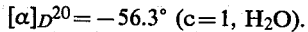 δppm: 2.3-4.3 (m, 8H), 7.4 (m, 5H).
mp: 105°-107° C.

EXAMPLE 2

Synthesis of para(sodiumoxycarbonyl)phenyl-β-D-xylopyranoside

To 300 ml. of acetonitrile, there were added 22.82 g. of methyl p-hydroxy benzoate and 52.15 g. of silver oxide, and further added 100 g. of anhydrous calcium sulfate. To the resulting reaction solution was added dropwise tri-O-acetyl-α-D-xylosylbromide (7) over one hour. After completion of the dropwise addition, the reaction mixture was filtered off, and the resulting filtrate was then concentrated under reduced pressure to obtain 61.5 g. of paramethoxycarbonylphenyl 2,3,4-tri-O-acetyl-β-D-xylopyranoside in the state of white needles.

To 200 ml. of anhydrous methanol was suspended 42.4 g. of the thus obtained paramethoxycarbonylphenyl 2,3,4-tri-O-acetyl-β-D-xylopyranoside (8), and 226 ml. of 1 N sodium hydroxide was added to the resulting suspension, followed by two hours' stirring at room temperature.

After passed through an acidic resin, the reaction mixture was brought to pH 7 by adding sodium hydroxide. The mixture solution was concentrated to dryness to yield 30 g. of the desired para(sodiumoxycarbonyl)phenyl-β-D-xylopyranoside in the state of white powder.

$[\alpha]_D^{20} = 31 34°$ (c=1, H$_2$O)
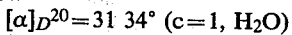 δppm: 3.2-4.3 (m, 5H), 5.2 (1H), 7.17, 7.93 (dd, J=8.4, 4H (φH)).

EXAMPLE 3

Synthesis of para(sodiumoxycarbonyl)phenyl 1-thio-β-D-xylopyranoside

To 19.8 g. of sodium salt of paracarboxythiophenol in dimethylformamide solution was added 29.5 g of tri-O-acetyl-α-D-xylosylchloride (4). After the resulting reaction mixture was allowed to stand overnight, the dimethylformamide was distilled away and the resulting residue was extracted with ethyl acetate. The obtained organic layer was washed with water, followed by drying over anhydrous magnesium sulfate. When the solvent was distilled away, white powdery paracarboxyphenyl 2,3,4-tri-O-acetyl-1-thio-β-D-xylopyranoside (10) was obtained. To 144 ml. of anhydrous methanol were added 12.0 g. of the obtained paracarboxyphenyl 2,3,4-tri-O-acetyl-1-thio-β-D-xylopyranoside (10) and 720 mg. of lithium hydroxide, and the mixture was allowed to stand overnight at room temperature. Then, the reaction mixture was diluted with water and was passed through an acidic resin in the usual way. The solution which has thus been passed was adjusted to pH 7.0 by adding sodium hydroxide. The so neutralized solution was concentrated to yield 8 g. of the desired para(sodiumoxycarbonyl)phenyl 1-thio-β-D-xylopyranoside in the state of white powder.

$[\alpha]_D^{20} = -49.5°$ (c=1, H$_2$O)
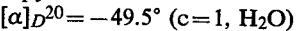 δppm: 3-4.3 (m, 5H), 4.83 (d, J=9.6, 1H), 7.6, 7.9 (dd, J=8.4, 4H (φ4)).

EXAMPLE 4

Synthesis of C-para(sodiumoxycarbonyl)benzyl-β-D-xylopyranoside

To an excess amount of p-bromobenzylmagnesiumbromide was added 11.78 g. of tri-O-acetyl-xylosylchloride (4) and, the reaction therebetween was carried out. The reaction mixture was poured into 500 ml. of water, followed by acidifying with acetic acid, and then the aqueous solution was extracted with ethyl acetate. The obtained organic layer, after washed with water, was dried over anhydrous magnesium sulfate. After the solvent was distilled away, 16 g. of anhydrous sodium acetate and 100 ml. of acetic anhydride were added to the resulting residue, and a reaction therebetween was carried out at 100° C. for one hour. Thereafter, the used solvent was distilled away, and then washing with water and drying were in turn carried out to yield 14.2 g. of white crystalline C-parabromobenzyl-2,3,4-tri-O-acetyl-β-D-xylopyranoside (12).

In 200 ml. of anhydrous methanol was suspended 14.2 g. of the obtained C-parabromobenzyl-2,3,4-tri-O-acetyl-β-D-xylopyranoside (12), and 400 mg. of lithium hydroxide was added to the resulting suspension. The reaction therebetween was carried out for one hour and the used solvent was distilled to obtain 11 g. of white crystalline C-parabromobenzyl-β-D-xylopyranoside (13).

To 11 g. of the obtained C-parabromobenzyl-β-D-xylopyranoside (13) were added excess benzyl chloride and potassium hydroxide to accomplish benzylation to the compound (13), whereby 9.3 g. of white crystalline C-parabromobenzyl-2,3,4-tri-O-benzyl-β-D-xylopyranoside (14) can be obtained.

Rieke's catalyst (a tetrahydrofuran solution of 3.37 g. of magnesium chloride, 5.35 g. of potassium iodide and 2.51 g. of metallic potassium) was added to 9.3 g. of the obtained C-parabromobenzyl-2,3,4-tri-O-benzyl-β-D-xylopyranoside (14), and the solution was heated under reflux for 4 hours. After completion of the reaction, the reaction mixture was cooled with ice-cold water and a dried carbonic acid gas was blown through the mixture. The reaction mixture was poured into ice water and was extracted with ether, and the resulting ethereal layer was dried over anhydrous magnesium sulfate. Then, the used solvent was distilled away to obtain 5.3 g. of oily C-paracarboxybenzyl-2,3,4-tri-O-benzyl-β-D-xylopyranoside (15).

To a mixture solution of 30 ml. of acetone, 30 ml. of methanol and 10 ml. of acetic acid was added 5.3 g. of the obtained C-paracarboxybenzyl-2,3,4-tri-O-benzyl-β-D-xylopyranoside (15) and further 0.92 g. of a 10% palladium-carbon, and a catalytic reduction was carried out. The solvent was distilled away and the residue was dissolved in 20 ml. of water. Sodium hydroxide was added to the aqueous solution to adjust its pH to 7.0, and then the solution was concentrated under reduced pressure to yield 2.8 g. of the desired C-para(sodium-oxycarbonyl)benzyl-β-D-xylopyranoside in the state of white powder.

$[\alpha]_D^{20} = -31.1°$ (c=1, H$_2$O)

IR(cm$^{-1}$): 1440, 1550, 1600, 3400

$^1$HNMR(D$_2$O), δppm: 2.3–4.1 (m, 8H), 7.44, 7.94 (dd, J=8.4, 4H (φH)).

EXAMPLE 5

Synthesis of N-paracarbamoylphenyl-D-xylopyranosylamine

To 30 ml. of water were added 15 g. (0.10 mol) of D-xylose and 14.05 g. (0.10 mol) of aminobenzamide, and 6 ml. of acetic acid was added dropwise to the solution under stirring over 5 minutes. After completion of the dropwise addition, the stirring operation was still continued to deposit a crystal and to solidify the whole solution. Then, it was allowed to stand at room temperature for one hour and was filtered with suction by use of a glass filter. After washing with a little cold water, the obtained white solid was dissolved in ethyl acetate, and the resulting solution was dried over anhydrous magnesium sulfate. The solvent was distilled away to obtain 20 g. of N-paracarbamoylphenyl-D-xylopyranosylamine in the state of white needles.

m.p.: 177°–178° C.

IR (KBr: cm$^{-1}$): 3500, 3400, 3340, 3280, 1650, 1615, 1055

NMR (δppm): 2.8–4.2 (m, 5H), 4.8 (m, 1H), 6.97 (d, 2H, J=8.6 Hz), 7.77 (d, 2H, J=8.6 Hz)

Nitrogen analysis (for C$_{12}$H$_{16}$O$_5$N$_2$): Found: 10.44%, Calcd: 10.45%.

EXAMPLE 6

Synthesis of n-heptyl 1-thio-β-D-xylopyranoside

To 20 ml. of a 50% aqueous acetone solution were added 2.92 g. of 2,3,4-tri-O-acetyl-1-thio-β-D-xylopyranoside (17) and 1.79 g. of n-heptyl bromide. To the solution was further added 1.38 g. of potassium carbonate and then a boiling under reflux was carried out for one hour. After completion of the reaction, the solution was neutralized with acetic acid, extracted with chloroform washed with water, and dried. The used solvent was distilled away to obtain 2.55 g. of colorless oily n-heptyl 2,3,4-tri-O-acetyl-1-thio-β-D-xylopyranoside (18). The yield was 65.3%.

The thus obtained n-heptyl 2,3,4-tri-O-acetyl-1-thio-β-D-xylopyranoside (18) was measured for specific rotatory power, infrared spectrum and NMR spectrum. The results are as follows:

$[\alpha]_D^{21} = -66.4°$ (c=1.38, CHCl$_3$)

IR (neat, cm$^{-1}$): 1755

$^1$HNMR(CDCl$_3$), δppm: 4.6 (1H, d, J=8 Hz, 1-H), 4.27 (1H, dd, J=5.6, 12 Hz, H-5e), 3.38 (1H, dd, J=9.2, 12 Hz, H-5a), 2.05 (3H, s), 2.07 (6H, s), 0.9 (3H, t), 1.33 (10H, m), 2.67 (2H, t), 4.8–5.5 (3H, m).

In 10 ml. of methanol was dissolved 2.45 g. of the compound (18), and 10 mg. of lithium hydroxide was added to the solution. The mixture was stirred at room temperature for one hour to yield the desired n-heptyl 1-thio-β-D-xylopyranoside which was a compound of the present invention. The yield was 95%.

IR (KBr, cm$^{-1}$): 3200–3500, 2920, 2850, 1045–1050

$^1$HNMR(CD$_3$OD), δppm: 0.9 (3H, t), 1.3 (10H, m), 2.67 (2H, t), 3–4.1 (5H, m), 4.32 (1H, d, J=9 Hz, H-1).

EXAMPLE 7

Synthesis of n-octyl 1-thio-β-D-xylopyranoside

In 20 ml. of methylene chloride were dissolved 2.92 g. of 2,3,4-tri-O-acetyl-1-thio-β-D-xylopyranoside (17) and 1.93 g. of n-octyl bromide, and 1.53 ml. of triethylamine was further added thereto. Then, the solution was stirred at room temperature for one day. After completion of the reaction, the reaction solution was washed with water and dried, and then the used solvent was distilled away to obtain 1.039 g. of colorless oily n-octyl-2,3,4-tri-O-acetyl-1-thio-β-D-xylopyranoside (18). The yield was 25.7%.

$[\alpha]_D^{21} = -60.1°$ (c=1.33, CHCl$_3$)

IR (neat, cm$^{-1}$): 1755

$^1$HNMR(CDCl$_3$), δppm: 4.6 (1H, d, J=8 Hz, H-1), 4.27 (1H, dd, J=5.6, 12 Hz), H-5e), 3.38 (1H, dd, J=9.2, 12 Hz, H-5e), 2.05 (6H, s), 2.07 (3H, s), 0.9 (3H, t), 1.33 (10H, m), 2.67 (2H, t), 4.8–5.5 (3H, m).

In 10 ml. of methanol was dissolved 2 g. of the thus obtained compound (18) and 15 mg. of lithium hydroxide was further added thereto, then the resulting mixture was stirred at room temperature for one hour to yield 1.32 g. of n-octyl 1-thio-β-D-xylopyranoside in the state of colorless needles. The yield was 95%.

IR (KBr, cm$^{-1}$): 3200–3500, 2920, 2850, 1045–1050.

EXAMPLE 8

Synthesis of n-lauryl 1-thio-β-D-xylopyranoside

By use of the same materials and in the same manner as in Example 6 except that n-heptyl bromide was replaced with 2.49 g. of n-lauryl bromide, there was obtained 2.3 g. of n-lauryl-2,3,4-tri-O-acetyl-1-thio-β-D-xylopyranoside (18) in the state of colorless needles. The yield was 50%.

mp: 52° C.

IR (KBr, cm$^{-1}$): 1745.

Next, this compound (18) was subjected to deacetylation in the same manner as in Example 6 to obtain n-lauryl 1-thio-β-D-xylopyranoside in the state of colorless needles. The yield was 90%.

IR (KBr, cm$^{-1}$): 3200–3500, 2920, 2850, 1045–1050.

EXAMPLE 9

Synthesis of n-stearyl 1-thio-β-D-xylopyranoside

By use of the same materials and in the same manner as in Example 6 except that n-heptyl bromide was replaced with 3.8 g. of n-steary iodide and the treatment time of a boiling under reflux was 1.5 hours, there was obtained 1.63 g. of n-stearlyl-2,3,4-tri-O-acetyl-1-thio-β-D-xylopyranoside (18) in the state of white powder. The yield was 30%.

mp: 60°–61° C.

IR (KBr, cm$^{-1}$): 1745.

Next, this compound (18) was treated in the same manner as in Example 6 to obtain n-stearyl 1-thio-β-D-xylopyranoside in the state of white powder. The yield was 85%.

IR (Kbr, cm$^{-1}$): 3200–3500, 2920, 2850, 1045–1050.

EXAMPLE 10

Synthesis of isopropyl 1-thio-β-D-xylopyranoside

To 20 ml. of 50% aqueous acetone solution were added 2.92 g. of 2,3,4-tri-O-acetyl-1-thio-β-D-xylopyranoside (17) and 1.38 g. of potassium carbonate. After 1.7 g. of isopropyl iodide was added dropwise to the resulting solution, two hours' stirring was carried out. After completion of the reaction, the same treatment as in Example 6 was given to obtain 1.98 g. of colorless oily isopropyl 1-thio-β-D-xylopyranoside (18). The yield was 96%. Rf (toluene: ethyl acetate=3:1): 0.43.

Next, this compound (18) was subjected to deacetylation in the same manner as in Example 6 to obtain 1.18 g. of isopropyl 1-thio-β-D-xylopyranoside in the state of colorless needles. The yield was 96%.

IR (KBr, cm$^{-1}$): 3370, 1045.

EXAMPLE 11

Synthesis of sec-butyl 1-thio-β-D-xylopyranoside

By use of the same materials and in the same manner as in Example 6 except that n-heptyl bromide was replaced with 1.37 g. of sec-butyl bromide and the treatment time of a boiling under reflux was 1.5 hours, there was 1.04 g. of colorless oily sec-butyl 2,3,4-tri-O-acetyl-1-thio-β-D-xylopyranoside (18). The yield was 30%. Rf (toluene:ethyl acetate=3:1): 0.50.

Next, this compound (18) was subjected to deacetylation in the same manner as in Example 6 to obtain 0.6 g. of sec-butyl 1-thio-β-D-xylopyranoside in the state of colorless needles. The yield was 90%.

IR (KBr, cm$^{-1}$): 3380, 1050

EXAMPLE 12

Synthesis of allyl 1-thio-β-D-xylopyranoside

By use of the same materials and in the same manner as in Example 10 except that isopropyl iodide was replaced with 1.68 g. of allyl iodide, there was obtained 3.32 g. of colorless oily allyl 2,3,4-tri-O-acetyl-1-thio-β-D-xylopyranoside (18). The yield was 100%. Rf (toluene:ethyl acetate=3:1): 0.48.

Next, this compound (18) was subjected to deacetylation in the same manner as in Example 6 to obtain 1.88 g. of allyl 1-thio-β-D-xylopyranoside in the state of colorless needles or flaky crystal. The yield was 91%.

IR (KBr, cm$^{-1}$): 3380, 1630, 1045.

EXAMPLE 13

By use of the same materials and in the same manner as in Example 6 except that n-heptyl bromide was replaced with n-nonyl bromide, n-decyl bromide, n-undecyl bromide, n-myristyl bromide, n-cetyl bromide, isobutyl bromide, isoamyl bromide, propargyl bromide, and isohexyl bromide, there were obtained n-nonyl 1-thio-β-D-xylopyranoside, n-decyl 1-thio-β-D-xylopyranoside, n-undecyl 1-thio-β-D-xylopyranoside, n-myristyl 1-chio-β-D-xylopyranoside, n-cetyl 1-thio-β-D-xylopyranoside, isobutyl 1-thio-β-D-xylopyranoside, isoamyl 1-thio-β-D-xylopyranoside, propargyl 1-thio-β-D-xylopyranoside and isohexyl 1-thio-β-D-xylopyranoside which were compounds of the present invention.

Next, the physicochemical properties of the β-D-xylopyranoside series compounds regarding the present invention were measured in view of their melting points, specific rotatory powers and Rf values by the use of a thin-layer chromatography (TLC) (stationary phase; silica gel and mobile phase; CHCl$_3$:MeOh=7:1). The results are shown in Table 1.

TABLE 1

| R | mp (°C.) | $[\alpha]_D^{21°}(°)$ | Rf |
|---|---|---|---|
| n-heptyl | 106 | −68.5 | 0.49 |
| n-octyl | 114 | −68.5 | " |
| n-nonyl | 119.5 | −64.8 | " |
| n-decyl | 121 | −62.5 | " |
| n-undecyl | 122 | −60.6 | 0.51 |
| n-lauryl | 123 | −52.0 | " |
| n-myristyl | 121 | −48.2 | " |
| n-cetyl | 118 | −45.7 | 0.53 |
| n-stearyl | 115 | −41.0 | 0.56 |
| isopropyl | 133.5 ∼ 134 | −85.0 | 0.35 |
| isobutyl | 97 ∼ 98 | −65.6 | 0.38 |
| sec-butyl | 125 ∼ 126 | −75.5 | " |
| isoamyl | 105 ∼ 106 | −73.9 | " |
| allyl | 89 ∼ 90 | −50.9 | 0.44* |
| propargyl | 139.5 ∼ 140.5 | −180.0 | 0.32 |
| isohexyl | 92 ∼ 93 | −53.4 | 0.44 |

*CHCl$_3$: MeOH = 5:1

EXAMPLE 14

Synthesis of C-n-heptyl-β-D-xylopyranoside(C-β-D-xylopyranosylheptane)

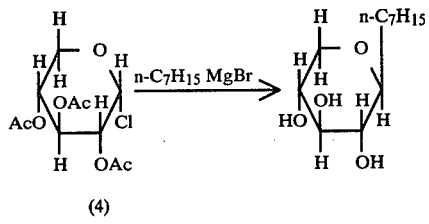

To an excess amount of an ethereal solution (300 ml.) of n-heptylmagnesium bromide, there was added dropwise, over 30 minutes, an ethereal solution (300 ml.) containing 23.9 g. (0.081 mole) of tri-O-acetyl-α-D-xylosyl chloride. After completion of the dropwise addition, the resulting reaction mixture was refluxed for 2 hours. After the reaction mixture was cooled to room temperature, it was poured gradually into 600 ml. of an icewater. The resulting mixture was acidified with acetic acid and then the aqueous layer was separated. After the thus obtained organic layer was concentrated under reduced pressure, followed by drying under reduced pressure to obtain a syrup. The so obtained syrup was subjected to silica gel column chromatography to yield 6 g. (yield: 31.9%) C-n-heptyl-β-D-xylopyranoside as the desired product.

$[\alpha]_D^{20} = -43.5°$ (c=1, CH$_3$OH)

$^1$HNMR(CD$_3$OD), δppm: 0.90 (t, 3H, CH$_3$), 1.1–2.0 (m, 12H, CH$_2$), 2.8–3.7 (m, 5H), 3.94 (dd, J=4.2, 10.0 Hz, 1H).

Melting point: 110°–111° C.

EXAMPLE 15

Synthesis of C-n-decyl-β-D-xylopyranoside(C-β-D-xylopyranosyldecane)

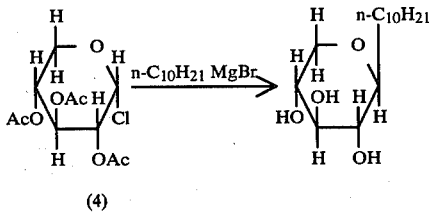

Following the procedure described in Example 1, an ethereal solution (300 ml.) containing 23.9 g. (0.081 mole) of tri-O-acetyl-α-D-xylosyl chloride was added dropwise to an excess amount of an ethereal solution (300 ml.) of n-desylmagnesium bromide and the mixture was subjected to reaction to yield 7.8 g. (yield: 35.1%) of C-n-decyl-β-D-xylopyranoside.

$[\alpha]_D^{20} = -33.0°$ (c=1, CH$_3$OH)

$^1$HNMR(CD$_3$OD), δppm: 0.90 (t, 3H, CH$_3$), 1.1–2.0 (m, 18H, CH$_2$), 2.8–3.7 (m, 5H), 3.94 (dd, J=4.2, 10.0 Hz, 1H).

Melting point: 90°–91° C.

EXAMPLE 16

Synthesis of C-n-myristyl-β-D-xylopyranoside(C-β-D-xylopyranosyltetradecane)

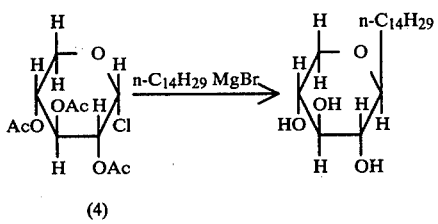

Following the procedure described in Example 1, an ethereal solution (150 ml.) containing 12.8 g. (0.043 mole) of tri-O-acetyl-α-D-xylosyl chloride was added dropwise to an excess amount of an ethereal solution (150 ml.) of n-myristylmagnesium bromide and the mixture was subjected to reaction to yield 6.0 g. (Yield: 42.3%) of C-n-myristyl-β-D-xylopyranoside.

$[\alpha]_D^{20} = -27.5°$ (c=1, CH$_3$OH)

$^1$HNMR(CD$_3$OD), δppm: 0.90 (t, 3H, CH$_3$), 1.1–2.0 (m, 26H, CH$_2$), 2.8–3.7 (m, 5H), 3.94 (dd, J=4.2, 10.0 Hz, 1H)

Melting point: 100°–101° C.

EXAMPLE 17

Synthesis of C-n-stearyl-β-D-xylopyranoside(C-β-D-xylopyranosyloctadecane)

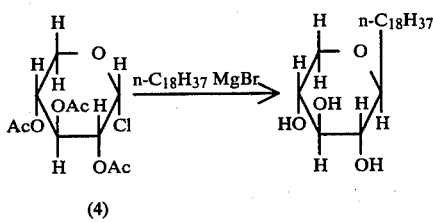

Following the procedure described in Example 1, an ethereal solution (200 ml.) containing 17.7 g. (0.060 mole) of tri-O-acetyl-α-D-xylosyl chloride was added dropwise to an excess amount of an ethereal solution (200 ml.) of n-stearylmagnesium bromide and the mixture was subjected to reaction to yield 8.8 g. (yield: 38.0%) of C-n-stearyl-β-D-xylopyranoside.

$[\alpha]_D^{20} = -25.0°$ (c=1, CH$_3$OH)

$^1$HNMR (CD$_3$OD), δppm: 0.90 (t, 3H, CH$_3$), 1.1–2.0 (m, 34H, CH$_2$), 2.8–3.7 (m, 5H), 3.94 (dd, J=4.2, 10.0 Hz, 1H)

Melting point: 98°–99° C.

Next, melting points, specific rotatory powers and Rf values on thin-layer chromatography(TLC) (stationary phase:silica gel, mobile phase:CHCl$_3$/CH$_3$OH (5/1) of the representative compounds according to the present invention, which have been prepared in the same manner as in the above-described Examples, are shown in Table 2.

TABLE 2

| Alkyl group | Melting point (°C.) | Specific rotatory power ($[\alpha]_D^{20}$, c = 1) $CH_3OH$) | Rf value |
|---|---|---|---|
| n-hexyl ($C_6$) | 105 ~ 106 | −54.5° | 0.441 |
| n-heptyl ($C_7$) | 110 ~ 111 | −43.5° | 0.447 |
| n-octyl ($C_8$) | 95 ~ 96 | −37.0° | 0.450 |
| n-nonyl ($C_9$) | 97 ~ 98 | −35.0° | 0.454 |
| n-decyl ($C_{10}$) | 90 ~ 91 | −33.0° | 0.461 |
| n-undecyl ($C_{11}$) | 94 ~ 95 | −31.0° | 0.464 |
| n-lauryl ($C_{12}$) | 93 ~ 94 | −30.0° | 0.467 |
| n-tridecyl ($C_{13}$) | 95 ~ 96 | −28.5° | 0.477 |
| n-myristyl ($C_{14}$) | 100 ~ 101 | −27.5° | 0.487 |
| n-pentadecyl ($C_{15}$) | 100 ~ 101 | −26.5° | 0.507 |
| n-cetyl ($C_{16}$) | 100 ~ 101 | −26.0° | 0.526 |
| n-heptadecyl ($C_{17}$) | 98 ~ 99 | −25.5° | 0.542 |
| n-stearyl ($C_{18}$) | 98 ~ 99 | −25.0° | 0.560 |

TEST EXAMPLE 1

Epiphysial cartilages were taken from chick embryos aged 12 days in the Tyrode's medium under ice-cooling, and excess tissues were removed therefrom. To 150 mg. of cartilages corresponding to five embryos, 5 ml. of BGJb [a completely synthetic culture medium prepared according to a recipe of GIBCO (Grand Island Biological Company)] was added, followed by pre-incubation at a temperature of 37° C. After replacing the culture medium, further 1 ml. of BGJb and 5 μCi $Na_2{}^{35}SO_4$ were added, and the culture system was kept at 37° C. for 3 hours. The culture medium was then replaced by 1 ml. of a fresh chase medium containing no radio active isotope. After keeping the culture system at 37° C. for 1 hour, the culture medium was separated from the tissues. To study the effects of the xyloside compound on the synthesis of glycosaminoglycan, the xyloside compound was added in the predetermined concentration to the pre-incubation and incubation media.

After the incubation, the labeled medium containing $Na_2{}^{35}SO_4$ was combined with the chase medium. Pronase-P (trade name) (available from Kaken Kagaku Co., Ltd.) was added thereto in a 0.5 M tris-HCl buffer solution (pH 8.0), and the resulting mixture was digested at 50° C. for 16 hours. The digested reaction mixture was then subjected to gel filtration through a column (1.5×14 cm.) packed with Bio-Gel P-2 (available from Bio-Rad Company) using a 0.2 M ammonium formate solution as an eluate. In this way, the $V_o$ fraction was collected and was then freeze-dried to give a crude glycosaminoglycan.

On the other hand, ice-cold 4 M guanidine hydrochloride was added to the tissues which were previously separated from the culture medium. The resulting mixture was left to stand overnight at a temperature of −20° C., and then homogenized. The obtained homogenate was left to stand overnight at room temperature and centrifuged at a speed of 8,500 rpm to obtain a supernatant. To the obtained liquid, water was added in an amount threefold that of the supernatant. Then, a 95% ethyl alcohol (containing 1.3% of potassium acetate) was added to the resulting mixture in an amount threefold that of the mixture to obtain a precipitate. This procedure was repeated twice, and the combined precipitates were dried in a desiccator. The obtained precipitates were dissolved in a 0.02 M tris-HCl buffer solution (pH 8.0) and digested with Pronase-P in the manner similar to the culture medium described above, thereby obtaining a crude glycosaminoglycan.

As the xyloside compound, conventional O-paranitrophenyl-β-D-xylopyranoside, and two compounds according to the present invention viz. C-n-butyl-β-D-xylopyranoside and C-ethyl-β-D-xylopyranoside were used. The effects of these xyloside compounds on the total amount of [$^{35}$S] glycosaminoglycan synthesized ($^{35}$S uptake amount), the amount thereof liberated to the culture medium and the amount thereof remaining in the tissues were as shown in FIGS. 1 to 3.

In each Figure, the vertical axis denotes the amount of [$^{35}$S]chondroitin sulfate ($^{35}$S cpm×$10^{-4}$/μmol.uronic acid) and the horizontal axis denotes the concentration (mM) of each xylopyranoside compound in the culture medium.

Referring to FIG. 1, the $^{35}$S uptake of glycosaminoglycan increased as the concentration of O-paranitrophenyl-β-D-xylopyranoside rose from 0.05 mM to 1.0 mM. At the concentration of 1 mM, the $^{35}$S uptake reached 40800 count per minute (cpm), the value which was 2.35 times that of the control. In this case, 95% of the control was liberated to the culture medium, while the amount of [$^{35}$S] glycosaminoglycan remaining in the tissues decreased to 11% of the control. This indicates that O-paranitrophenyl-β-D-xylopyranoside is extremely effective as an initiator for the synthesis of chondroitin sulfate as reported in J. Biochem., 74, 1069–1073 (1973).

Figure 3:
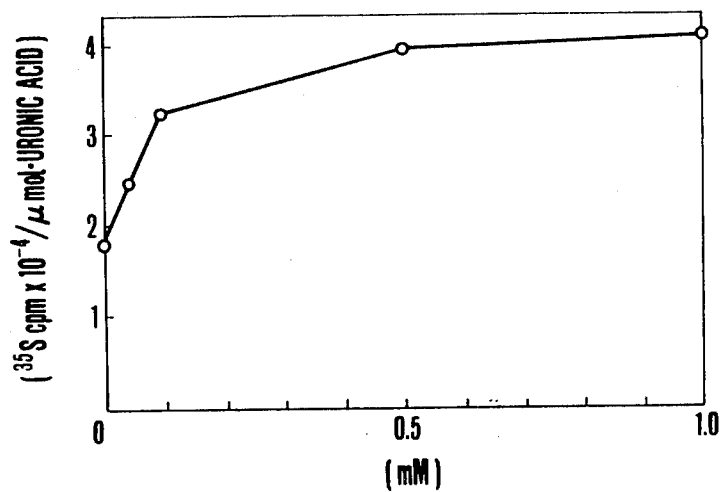

On the other hand, with respect to the C-β-D-xylopyranosides of the present invention, the test results were as shown in FIGS. 2 and 3. As shown in these Figures, the total $^{35}$S uptake amount of glycosaminoglycan increased as the concentration of the xyloside compounds rose, like the conventional compound described above. At the same time, the amount of [$^{35}$S] glycosaminoglycan liberated into the culture medium increased, while the amount thereof remaining in the tissues decreased. This indicates that, although a higher concentration of the C-β-D-xylopyranosides of the present invention is required compared with the conventional O-β-D-xylopyranoside compound, the compounds according to the present invention are excellent initiators for the synthesis of chondroitin sulfate.

TEST EXAMPLE 2

According to the same procedure as in Test example 1, a crude glycosaminoglycan was obtained.

As the xyloside compound, conventional O-paranitrophenyl β-D-xylopyranoside and N-para(sodiumoxycarbonyl)phenyl-D-xylopyranosylamine, and three compounds according to the present invention viz. para(sodiumoxycarbonyl)phenyl β-D-xylopyranoside, C-para(sodiumoxycarbonyl)benzyl-β-D-xylopyranoside and para(sodiumoxycarbonyl)phenyl 1-thio-β-D-xylopyranoside were used. The effects of these xyloside compounds on the total amount of [$^{35}$S]glycosaminoglycan synthesized ($^{35}$S uptake amount) were shown in FIGS. 3 to 7.

In each Figure, the vertical axis denotes the amount of [$^{35}$S]chondroitin sulfate ($^{35}$S cpm×$10^{-4}$/μmol.uronic acid), and the horizontal axis denotes the concentration (mM) of each xylopyranoside compound in the culture medium.

Referring to FIG. 3, the $^{35}$S uptake of glycosaminoglycan increased as the concentration of O-paranitrophenyl-β-D-xylopyranoside rose from 0.05 mM to 1.0 mM. At the concentration of 1 mM, the $^{35}$S uptake reached 40800 count per minute (cpm), the value which was 2.35 times that of the control. In this case, 95% of the control was liberated to the culture medium, while the amount of [35S] glycosaminoglycan remaining in the tissues decreased to 11% of the control. This indicates that O-paranitrophenyl-β-D-xylopyranoside is extremely effective as an initiator for the synthesis of chondroitin sulfate as reported in J. Biochem., 74, 1069–1073 (1973).

Figure 4:
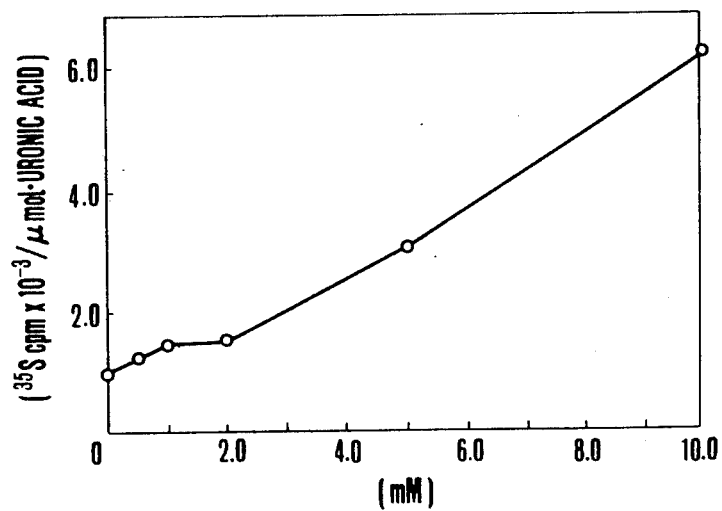

FIG. 4 indicates that N-para(sodiumoxycarbonyl)-phenyl-D-xylopyranosylamine shows a similar tendency, although it requires higher concentrations as compared with O-paranitrophenyl-β-D-xylopyranoside.

Figure 5:
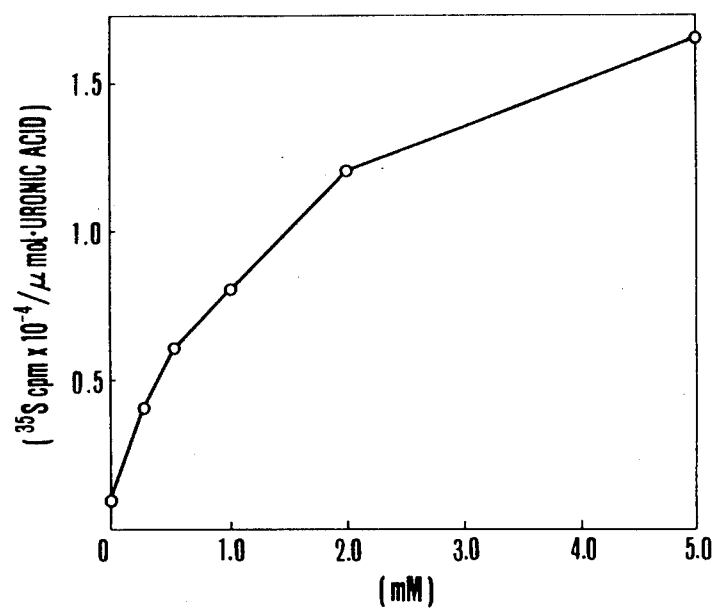
Figure 6:
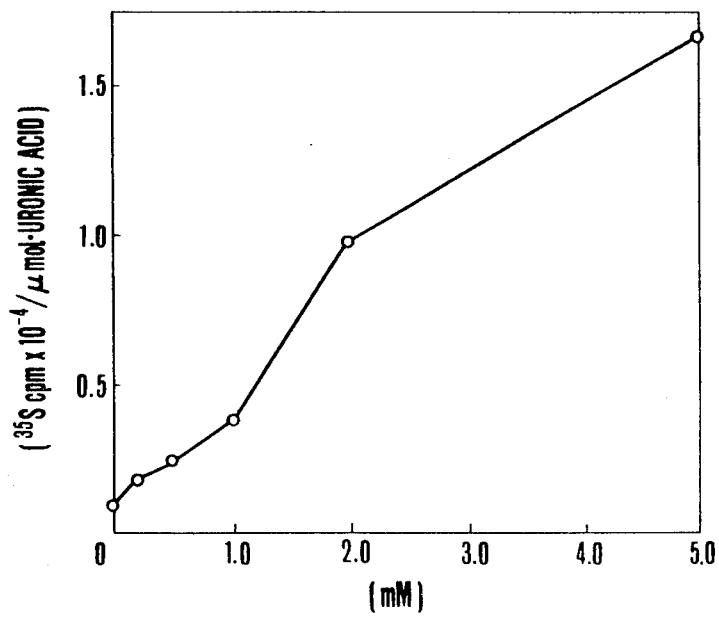
Figure 7:
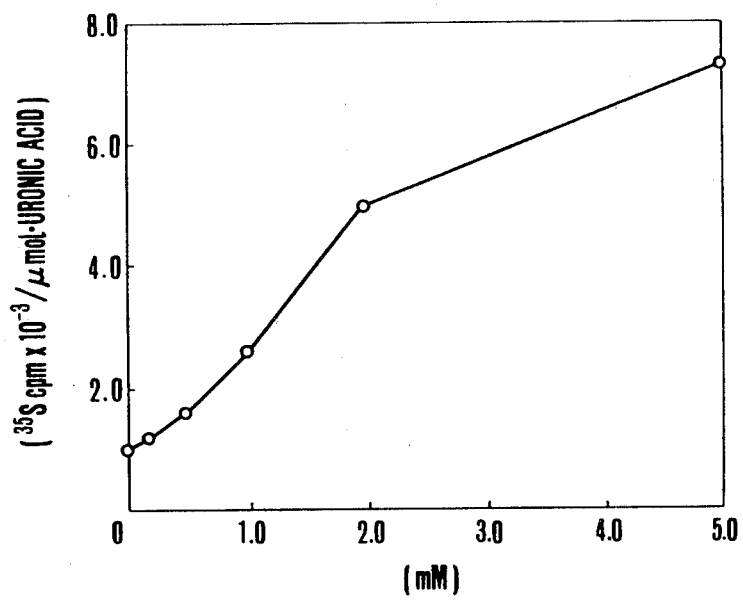

On the other hand, with respect to the compounds of the present invention, the test results were as shown in FIGS. 5 to 7. As shown in these Figures, the total $^{35}$S uptake amount of glycosaminoglycan increased as the concentration of the xyloside compounds rose, like the conventional compound described above. At the same time, the amount of [35S] glycosaminoglycan liberated into the culture medium increased, while the amount thereof remaining in the tissues decreased. In particular, when the curves in FIGS. 4 to 7 are compared with each other carefully, it may be found that the total uptake amount of [35S]chondroitin sulfate of the case where N-para(sodiumoxycarbonyl)phenyl-D-xylopyranosylamine is used does not change remarkably within the range of the concentration of 0 to 20 mM of the compound and that the increase in the total uptake amount thereafter is mild. In contrast thereto, in cases of the compounds as shown in FIGS. 5 to 7, the increase in the total uptake amount of [35S]chondroitin sulfate can already be observed at a concentration of not more than 0.5 mM or of not more than 1.0 mM of the compound. Further, it can be found that the total uptake amount increases drastically within the range of up to 2.0 mM.

This indicates that the compounds according to the present invention influences the synthesis of chondroitin sulfate at a lower concentration as compared with conventional N-para(sodiumoxycarbonyl)phenyl-D-xylosylamine, i.e., at a concentration of around 1/5 to ½ of the former relative to the latter compound, and that the compounds according to the present invention are excellent initiators for the synthesis of chondroitin sulfate.

TEST EXAMPLE 3

According to the same procedure as in Test example 1, a crude glycosaminoglycan was obtained.

As the xyloside compound, conventional O-paranitrophenyl β-D-xylopyranoside and N-paracarbamoyl-phenyl-D-xylopyranosylamine of the present invention were used. The effects of these xyloside compounds on the total amount of [35S]glycosaminoglycan synthesized (35S uptake amount) were shown in FIGS. 8 and 9.

Referring to FIG. 8, the $^{35}$S uptake of glycosaminoglycan increased as the concentration of O-paranitrophenyl-β-D-xylopyranoside rose from 0.05 mM to 1.0 mM. At the concentration of 1 mM, the $^{35}$S uptake reached 40800 count per minute (cpm), the value which was 2.35 times that of the control. In this case, 95% of the control was liberated to the culture medium, while the amount of [35S]glycosaminoglycan remaining in the tissues decreased to 11% of the control. This indicates that O-paranitrophenyl-β-D-xylopyranoside is extremely effective as the initiator for the synthesis of condroitin sulfate as reported in J. Biochem., 74, 1069–1073 (1973).

On the other hand, with respect to N-carbamoylphenyl-D-xylopyranosylamine of the present invention, the test results were shown in FIG. 9. As shown in FIG. 9, $^{35}$S uptake amount of glycosaminoglycan increased as the concentration of the xyloside compound rose, like the conventional compound described above. This indicates that N-carbamoylphenyl-D-xylopyranosylamine of the present invention is a good initiator for the synthesis of chondroitin sulfate, although it requires higher concentration as compared with the O-β-D-xylopyranoside compounds.

TEST EXAMPLE 4

According to the same procedure as in Test example 1, a crude glycosaminoglycan was obtained.

As the xyloside compound, publicly-known methyl 1-thio-β-D-xylopyranoside and n-butyl 1-thio-β-D-xylopyranoside, and six compounds according to the present invention viz. n-heptyl 1-thio-β-D-xylopyranoside, n-nonyl 1-thio-β-D-xylopyranoside, n-decyl 1-thio-β-D-xylopyranoside, n-undecyl 1-β-D-xylopyranoside, n-lauryl 1-thio-β-D-xylopyranoside and n-cetyl 1-thio-β-D-xylopyranoside were used. The effects of these compounds on the total amount of [35S]glycosaminoglycan synthesized (35S uptake amount) were investigated.

That is, after the effect of the addition of DMSO (dimethyl sulfoxide) which is a solvent was investigated, cycloheximide was added to the medium so that the final concentration thereof might be 0.03 mM, thereby inhibiting the synthesis of [35S]glycosaminoglycan by around up to 95%. Subsequently, to the medium in which the synthesis of glycosaminoglycan had been inhibited, there was added each solution of the xyloside compound in DMSO having various concentrations to investigate the recovery in the rate of the $^{35}$S uptake (the relative value expressed by percentage $^{35}$S uptake relative to the amount of uptake in a control medium to which no xylpyranoside compound was added). The results are shown in Table 3.

TABLE 3

| Substances added to the medium and their concentration | | | |
|---|---|---|---|
| Inhibitor, conc. (mM) | Xyloside compd., conc. (mM) | Final conc. of DMSO (%) | Rate of $^{35}$S uptake (%) |
| Examples — | — | 0 | 100 |
| — | — | 0.1 | 119.1 |
| — | — | 0.2 | 95.4 |
| — | — | 0.5 | 90.6 |
| — | — | 1.0 | 96.3 |
| cyclohex-imide 0.3 | — | 0 | 5.5 |
| cyclohex-imide 0.3 | — | 0.1 | 4.9 |
| cyclohex-imide 0.3 | — | 0.2 | 6.1 |
| cyclohex-imide 0.3 | — | 0.5 | 6.1 |
| cyclohex-imide 0.3 | — | 1.0 | 5.8 |

As is clear from Table 3, when DMSO is added to the medium so that the final concentration thereof in the medium might be 0.1 to 1.0%, the rate of $^{35}$S uptake became ±10% which is a small variation. In cases where cycloheximide, which is an inhibitor of the synthesis of $^{35}$S glycosaminoglycan, was added further thereto, the rate was reduced to around 5 to 6%.

When 0.02 to 0.10 mM of a solution of the xyloside compound according to the present invention in DMSO was added further to the resulting medium, the rate of $^{35}S$ uptake was recovered up to at least 10%. In cases where n-heptyl 1-thio-$\beta$-D-xylopyranoside or n-octyl 1-$\beta$-D-xylopyranoside was used even as a 0.02 mM solution in DMSO, the $^{35}S$ uptake was around twice as compared with the case where no such xylopyranoside was added (control). This indicates that the compounds according to the present invention are better initiator as compared with methyl 1-thio-$\beta$-D-xylopyranoside or n-butyl 1-thio-$\beta$-D-xylopyranoside, both of which are a known compound.

TEST EXAMPLE 5

According to the same procedure as in Example 1, a crude glycosaminoglycan was obtained.

As the xylopyranoside compound, there were used C-n-hexyl-$\beta$-D-xylopyranoside, C-n-heptyl-$\beta$-D-xylopyranoside, C-n-octyl-$\beta$-D-xylopyranoside, C-n-nonyl-$\beta$-D-xylopyranoside, C-n-lauryl-$\beta$-D-xylopyranoside and C-n-cetyl-$\beta$-D-xylopyranoside according to the present invention, and the effects of these compounds on the total amount of $^{35}S$ glycosaminoglycan synthesizsed ($^{35}S$ uptake amount) were investigated.

That is, after the effect of the addition of DMSO which is a solvent was investigated, cycloheximide was added to the medium so that the final concentration might be 0.03 mM to inhibit the synthesis of $^{35}S$ glycosaminoglycan by around up to 95%. Subsequently, each solution in DMSO having various concentrations of the xyloside compounds was added to the medium in which the synthesis of glycosaminoglycan was inhibited, and the recovery in the rate of the $^{35}S$ uptake (a relative value expressed by percentage of a $^{35}S$ uptake relative to the uptake in a medium where no xyloside compound was included) was observed.

The results are shown in Table 4.

TABLE 4

| | Substances added to the medium and their concentration | | |
|---|---|---|---|
| Final conc. of inhibitor (mM) | Xyloside compd., conc. (mM) | Final conc. of DMSO (%) | Rate of $^{35}S$ uptake (%) |
| Examples — | — | 0 | 100 |
| — | — | 0.1 | 119.1 |
| — | — | 0.2 | 95.4 |
| — | — | 0.5 | 90.6 |
| — | — | 1.0 | 96.3 |
| cyclohex-imide 0.3 | — | 0 | 5.5 |
| cyclohex-imide 0.3 | — | 0.1 | 4.9 |
| cyclohex-imide 0.3 | — | 0.2 | 6.1 |
| cyclohex-imide 0.3 | — | 0.5 | 6.1 |
| cyclohex-imide 0.3 | — | 1.0 | 5.8 |
| cyclohex-imide 0.3 | C-n-hexyl-$\beta$-D-xylopyranoside 0.2 | 0.1 | 82.0 |
| cyclohex-imide 0.3 | C-n-hexyl-$\beta$-D-xylopyranoside 0.5 | 0.1 | 148.0 |
| cyclohex-imide 0.3 | C-n-hexyl-$\beta$-D-xylopyranoside 1.0 | 0.1 | 196.0 |
| cyclohex-imide 0.3 | C-n-heptyl-$\beta$-D-xylopyranoside 0.2 | 0.1 | 114.0 |
| cyclohex-imide 0.3 | C-n-heptyl-$\beta$-D-xylopyranoside 0.5 | 0.1 | 183.0 |
| cyclohex-imide 0.3 | C-n-heptyl-$\beta$-D-xylopyranoside 1.0 | 0.1 | 193.0 |

TABLE 4-continued

| | Substances added to the medium and their concentration | | |
|---|---|---|---|
| Final conc. of inhibitor (mM) | Xyloside compd., conc. (mM) | Final conc. of DMSO (%) | Rate of $^{35}S$ uptake (%) |
| imide 0.3 | xylopyranoside 1.0 | | |

As is clear from Table 3, when DMSO is added to the medium so that the final concentration thereof in the medium might be 0.1 to 1.0%, the rate of $^{35}S$ uptake became ±10% which is a small variation. In cases where cycloheximide, which is an inhibitor of the synthesis of $^{35}S$ glycosaminoglycen, was added further thereto, the rate was reduced to around 5 to 6%.

When a solution in DMSO of the xyloside compound according to the present invention was added to the resultant medium in an amount of 0.2 to 1.0 mM, even if the compound shows lower $^{35}S$ uptake amount, the uptake amount was recovered up to 68% by selecting the amount of usage. This indicates that C-n-hexy-$\beta$-D-xylopyranoside and C-n-heptyl-$\beta$-D-xylopyranoside are extremely effective initiators for the synthesis of chondroitin sulfate when they are used as a 1.0 mM solution in DMSO.

TEST EXAMPLE 6

Toxicity of the compound according to this invention

The acute toxicity of the compound according to this invention was determined by forced oral or intraperitoneal administration thereof to ddY mice.

To prepare each specimen to be administered, a predetermined amount of each compound shown in Table 5 was dissolved in a physiological saline or suspended in a 0.2% solution of carboxymethylcellulose in a physiological saline. Each specimen was administered orally to a ddY mouse via its stomach tube or injected intraperitoneally.

The presence or absence of the symptoms of death was observed for 7 days after administration, and $LD_{50}$ of each compound was determined from the mortality accumulated to the 7th day of the administration, according to the graphic method of Litchfield-Wilcoxon.

The results are shown in Table 5.

TABLE 5

| | $LD_{50}$ through oral (po) or intraperitoneal (ip) administration | |
|---|---|---|
| Compound | $LD_{50}$(po) (mg/kg body weight) | $LD_{50}$(ip) (mg/kg body weight) |
| C-para(lithiumoxycarbonyl)benzyl-$\beta$-D-xylopyranoside | 8600 | 2500 |
| C-para(sodiumoxycarbonyl)benzyl-$\beta$-D-xylopyranoside | 9300 | 3000 |
| Para(lithiumoxycarbonyl)phenyl 1-thio-$\beta$-D-xylopyranoside | 7800 | 2700 |
| Para(sodiumoxycarbonyl)phenyl 1-thio-$\beta$-D-xylopyranoside | 7000 | 2600 |
| Para(potassiumoxycarbonyl)phenyl-$\beta$-D-xylopyranoside | 9800 | 3020 |
| Para(sodiumoxycarbonyl)phenyl-$\beta$-D-xylopyranoside | 8200 | 2800 |
| C-Benzyl-1-$\beta$-D-xylopyranoside | 7200 | 2400 |
| C-n-Heptyl-$\beta$-D-xylopyranoside | 4200 | 1040 |
| C-n-Nonyl-$\beta$-D-xylopyranoside | 3000 | 920 |
| C-n-Lauryl-$\beta$-D-xylopyranoside | 2800 | 620 |
| C-n-Stearyl-$\beta$-D-xylopyranoside | 2500 | 480 |
| C-n-Eicosyl-$\beta$-D-xylopyranoside | 2620 | 430 |

TABLE 5-continued

| | LD$_{50}$ through oral (po) or intraperitoneal (ip) administration | |
|---|---|---|
| Compound | LD$_{50}$(po) (mg/kg body weight) | LD$_{50}$(ip) (mg/kg body weight) |
| Isopropyl 1-thio-β-D-xylopyranoside | 6700 | 2200 |
| Isoamyl 1-thio-β-D-xylopyranoside | 5800 | 1850 |
| n-Decyl 1-thio-β-D-xylopyranoside | 2500 | 450 |
| n-Lauryl 1-thio-β-D-xylopyranoside | 2300 | 407 |
| n-Cetyl 1-thio-β-D-xylopyranoside | 2280 | 425 |
| n-Eicosyl 1-thio-β-D-xylopyranoside | 2300 | 400 |

TEST EXAMPLE 7

Activity against a transplantable cancer, Sarcoma-180

Sarcoma-180 cells (1×10$^6$ cells) were inoculated subcutaneously into the back skin of each of ICR-JCL mice.

Chemotherapy was given intraperitoneally 24 hrs. after inoculation and performed once a day for 10 days. Each specimen to be administered was prepared by dissolving or suspending 30 mg of each compound according to this invention in 1 ml of a physiological saline or in 1 ml of a 0.2% solution of carboxymethylcellulose in a physiological saline, respectively.

All the solutions and the suspensions thus prepared were injected at a volume of 0.1 ml as a single dose (100 mg/Kg).

The activity against Sarcoma-180 was evaluated in terms of the inhibition ratio (I.R.) (%) and shown in Table 6.

The inhibition ratio (%) was calculated according to the following equation:

I.R. = (1 − T/C) × 100% wherein T represents the mean weight of the tumor Sarcoma-180 in a tested group of mice; and C represents the mean weight of the tumor in a control group of mice.

TABLE 6

| Activity against Sarcoma-180 | |
|---|---|
| Compound | I.R. (%) |
| C-para(lithiumoxycarbonyl)benzyl-β-D-xylopyranoside | 44.7 |
| C-para(sodiumoxycarbonyl)benzyl-β-D-xylopyranoside | 53.2 |
| Para(lithiumoxycarbonyl)phenyl 1-thio-β-D-xylopyranoside | 47.2 |
| Para(sodiumoxycarbonyl)phenyl 1-thio-β-D-xylopyranoside | 49.6 |
| Para(potassiumoxycarbonyl)phenyl-β-D-xylopyranoside | 44.8 |
| Para(sodiumoxycarbonyl)phenyl-β-D-xylopyranoside | 39.7 |
| C-Benzyl-1-β-D-xylopyranoside | 30.9 |
| C-n-Heptyl-β-D-xylopyranoside | 54.8 |
| C-n-Nonyl-β-D-xylopyranoside | 73.1 |
| C-n-Lauryl-β-D-xylopyranoside | 83.4 |
| C-n-Stearyl-β-D-xylopyranoside | 54.6 |
| C-n-Eicosyl-β-D-xylopyranoside | 44.3 |
| Isopropyl 1-thio-β-D-xylopyranoside | 30.4 |
| Isoamyl 1-thio-β-D-xylopyranoside | 35.6 |
| n-Decyl 1-thio-β-D-xylopyranoside | 40.0 |
| n-Lauryl 1-thio-β-D-xylopyranoside | 42.3 |
| n-Cetyl 1-thio-β-D-xylopyranoside | 34.7 |
| n-Eicosyl 1-thio-β-D-xylopyranoside | 32.2 |

As is clear from Table 6, it can be understood that all the compounds of this invention exhibit the activity against Sarcoma-180.

From the data of LD$_{50}$ and I.R. as shown above, it can be understood that the transplantable cancer by Sarcoma-180 in mice is inhibited or alleviated by 50% by administering one of the compounds according to this invention in a dose of about 100 mg/kg body weight per day through interperitoneal administration.

TEST EXAMPLE 8

Inhibitory effect against platelet agglutinating agents

Inhibitory activities of each compound of this invention against platelet agglutinating agents (ADP, collagen, thrombin, ristocetin and epinephrine) were investigated according to the method using a microscope.

(1) Preparation of PRP (Platelet Rich Plasma)

PRP was prepared by mixing a 3.8% aqueous sodium citrate and a human vein blood at a ratio of 1:9; centrifuging the mixture at 700 r.p.m. for 10 minutes; and then collecting the supernatant.

(2) Preparation of PPP (Platelet Poor Plasma)

The residue remaining after collection of the PRP mentioned above was subjected further to centrifugation at 3000 r.p.m. for 10 minutes and then collected the supernatant to obtain PPP.

(3) Platelet agglutinating agents

Following solutions were employed for the test.

| a. | ADP | (2 μM/ml solution) |
| b. | collagen | (0.25 μM/ml solution) |
| c. | thrombin | (0.25 U/ml solution) |
| d. | ristocetin | (1.5 mg/ml solution) |
| e. | epinephrine | (2 μg/ml solution) |

(4) Test procedure

In each well of a Multidish (Nunc Multidish having 24 wells) was placed 0.2 ml of PRP (containing 3.0×10$^5$ platelet cells/cmm).

Thereto was added 50 μl of a specimen solution containing 10 mM of the compound according to this invention, and the mixture was stirred at 37° C. for 2 minutes. To the mixture was added 10 μl of each solution of the platelet agglutinating agent mentioned above, and the result was observed by using a microscope 1 minute and then 5 minutes thereafter.

The degree of agglutination was expressed by using marks +, ++, +++, etc., according to the method by Fukutake et al [Katsuhiro Fukutake, Iwao Yamaguchi: Blood and Blood Vessel, Volume 6, No. 7, pp. 55–60 (1975)].

TABLE 7

| | | | State of agglutination | |
|---|---|---|---|---|
| Specimen | (conc.) | Agglutinant | 1 min. | 5 min. |
| Control | (0) | ADP | ++ | +++ |
| | (0) | collagen | ++ | ++ |
| | (0) | thrombin | ++ | ++ |
| | (0) | ristocetin | ++ | ++ |
| | (0) | epinephrine | ++ | ++ |
| 50% Ethanol | (0) | ADP | ++ | +++ |
| | (0) | collagen | ++ | ++ |
| | (0) | thrombin | ++ | ++ |
| | (0) | ristocetin | ++ | ++ |
| | (0) | epinephrine | ++ | ++ |
| C-para(sodium-oxycarbonyl)benzyl-β-D-xylopyranoside | (100 mM) | ADP | ± | ± |
| | (100 mM) | collagen | ± | ± |
| | (100 mM) | thrombin | ± | ± |
| | (100 mM) | ristocetin | ± | ± |

TABLE 7-continued

| Specimen | (conc.) | Agglutinant | State of agglutination 1 min. | 5 min. |
|---|---|---|---|---|
| Para(sodium-oxycarbonyl)phenyl 1-thio-β-D-xylopyranoside | (100 mM) | epinephrine | ± | ± |
| | (100 mM) | ADP | ± | ± |
| | (100 mM) | collagen | ± | ± |
| | (100 mM) | thrombin | ± | ± |
| | (100 mM) | ristocetin | ± | ± |
| Para(sodium-oxycarbonyl)phenyl-β-D-xylopyranoside | (100 mM) | epinephrine | ± | ± |
| | (100 mM) | ADP | ± | ± |
| | (100 mM) | collagen | ± | ± |
| | (100 mM) | thrombin | ± | ± |
| | (100 mM) | ristocetin | ± | ± |
| C-Benzyl-1-β-D-xylopyranoside | (100 mM) | epinephrine | ± | ± |
| | (10 mM) | ADP | ± | ± |
| | (10 mM) | collagen | ± | ± |
| | (10 mM) | thrombin | ± | ± |
| | (10 mM) | ristocetin | ± | ± |
| C-n-Heptyl-β-D-xylopyranoside* | (10 mM) | epinephrine | ± | ± |
| | (5 mM) | ADP | ± | ± |
| | (5 mM) | collagen | ± | ± |
| | (5 mM) | thrombin | ± | ± |
| | (5 mM) | ristocetin | ± | ± |
| C-n-Nonyl-β-D-xylopyranoside* | (5 mM) | epinephrine | ± | ± |
| | (2 mM) | ADP | ± | + |
| | (2 mM) | collagen | ± | + |
| | (2 mM) | thrombin | ± | + |
| | (2 mM) | ristocetin | ± | + |
| C-n-Lauryl-β-D-xylopyranoside* | (2 mM) | epinephrine | ± | ± |
| | (2 mM) | ADP | ± | ± |
| | (2 mM) | collagen | ± | + |
| | (2 mM) | thrombin | ± | + |
| | (2 mM) | ristocetin | ± | + |
| C-n-Stearyl-β-D-xylopyranoside* | (2 mM) | epinephrine | ± | ± |
| | (2 mM) | ADP | ± | + |
| | (2 mM) | collagen | ± | + |
| | (2 mM) | thrombin | ± | + |
| | (2 mM) | ristocetin | ± | + |
| C-n-Eicosyl-β-D-xylopyranoside* | (2 mM) | epinephrine | ± | ± |
| | (2 mM) | ADP | ± | + |
| | (2 mM) | collagen | ± | + |
| | (2 mM) | thrombin | ± | + |
| | (2 mM) | ristocetin | ± | + |
| Isopropyl 1-thio-β-D-xylopyranoside | (2 mM) | epinephrine | ± | ± |
| | (5 mM) | ADP | ± | ± |
| | (5 mM) | collagen | ± | ± |
| | (5 mM) | thrombin | ± | ± |
| | (5 mM) | ristocetin | ± | ± |
| Isoamyl 1-thio-β-D-xylopyranoside | (5 mM) | epinephrine | ± | ± |
| | (5 mM) | ADP | ± | ± |
| | (5 mM) | collagen | ± | ± |
| | (5 mM) | thrombin | ± | ± |
| | (5 mM) | ristocetin | ± | ± |
| n-Decyl 1-thio-β-D-xylopyranoside* | (5 mM) | epinephrine | ± | ± |
| | (2 mM) | ADP | ± | + |
| | (2 mM) | collagen | ± | + |
| | (2 mM) | thrombin | ± | + |
| | (2 mM) | ristocetin | ± | + |
| n-Lauryl 1-thio-β-D-xylopyranoside* | (2 mM) | epinephrine | ± | + |
| | (2 mM) | ADP | ± | + |
| | (2 mM) | collagen | ± | + |
| | (2 mM) | thrombin | ± | + |
| | (2 mM) | ristocetin | ± | + |
| n-Cetyl 1-thio-β-D-xylopyranoside* | (2 mM) | epinephrine | ± | ± |
| | (2 mM) | ADP | ± | + |
| | (2 mM) | collagen | ± | + |
| | (2 mM) | thrombin | ± | + |
| | (2 mM) | ristocetin | ± | + |
| n-Eicosyl 1-thio-β-D-xylopyranoside* | (2 mM) | epinephrine | ± | ± |
| | (2 mM) | ADP | ± | + |
| | (2 mM) | collagen | ± | + |
| | (2 mM) | thrombin | ± | + |
| | (2 mM) | ristocetin | ± | + |
| | (2 mM) | epinephrine | ± | ± |

*dissolved in 50% ethanol

We claim:

1. A D-xylopyranoside series compound of the formula:

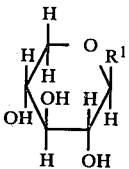

in which $R^1$ is selected from the group consisting of

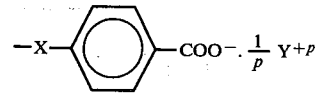

wherein X is selected from the group consisting of oxygen, sulfur and a methylene group; y is selected from the group consisting of hydrogen, lithium, sodium, potassium, magnesium, calcium and aluminum; and p represents the valency of an atom represented by Y;

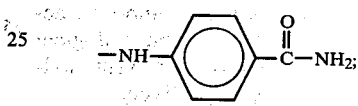

—S—$R^2$ wherein $R^2$ is selected from the group consisting of a straight-chain alkyl group having from 9 to 25 carbon atoms, a branched alkyl group having from 3 to 25 carbon atoms, a straight-chain alkenyl group having 3 to 25 carbon atoms, a branched alkenyl group having from 3 to 25 carbon atoms, a straight-chain alkynyl group having 3 to 25 carbon atoms and a branched alkynyl group having from 3 to 25 carbon atoms; and an alkyl group having from 6 to 25 carbon atoms.

2. The D-xylopyranoside series compound of claim 1, wherein the alkyl group represented by $R^1$ is selected from the group consisting of n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-henicosyl, n-docosyl, n-tricosyl, n-tetracosyl and n-pentacosyl.

3. The D-xylopyranoside series compound of claim 1, wherein $R^2$ is selected from the group consisting of a straight-chain alkyl group having from 9 to 18 carbon atoms, a branched alkyl group having from 3 to 18 carbon atoms, an alkenyl group having from 3 to 18 carbon atoms, and an alkynyl group having from 3 to 18 carbon atoms.

4. The D-xylopyranoside series compound of claim 1 selected from the group consisting of the following compounds:
Paracarboxyphenyl-β-D-xylopyranoside
Paracarboxyphenyl 1-thio-β-D-xylopyranoside
C-Paracarboxybenzyl-β-D-xylopyranoside [4-(C-β-D-xylopyranosyl)methyl-1-benzoic acid]
Para(lithiumoxycarbonyl)phenyl-β-D-xylopyranoside
Para(lithiumoxycarbonyl)phenyl 1-thio-β-D-xylopyranoside
C-Para(lithiumoxycarbonyl)benzyl-β-D-xylopyranoside [lithium 4-(C-β-D-xylopyranosyl)methyl-1-benzoate]
Para(sodiumoxycarbonyl)phenyl-β-D-xylopyranoside Para(sodiumoxycarbonyl)phenyl 1-thio-β-D-xylopyranoside
C-Para(sodiumoxycarbonyl)benzyl-β-D-xylopyranoside [sodium 4-(C-β-D-xylopyranosyl)methyl-1-benzoate]
Para(potassiumoxycarbonyl)phenyl-β-D-xylopyranoside
Para(potassiumoxycarbonyl)phenyl 1-thio-β-D-xylopyranoside
C-Para(potassiumoxycarbonyl)benzyl-β-D-xylopyranoside [potassium 4-(C-β-D-xylopyranosyl)methyl-1-benzoate]
Para(magnesiumoxycarbonyl)phenyl-β-D-xylopyranoside
Para(magnesiumoxycarbonyl)phenyl 1-thio-β-D-xylopyranoside
C-Para(magnesiumoxycarbonyl)benzyl-β-D-xylopyranoside [magnesium 4-(C-β-D-xylopyranosyl)methyl-1-benzoate]
Para(calciumoxycarbonyl)phenyl-β-D-xylopyranoside
Para(calciumoxycarbonyl)phenyl 1-thio-β-D-xylopyranoside
C-Para(calciumoxycarbonyl)benzyl-β-D-xylopyranoside [calcium 4-(C-β-D-xylopyranosyl)methyl-1-benzoate]
Para(aluminiumoxycarbonyl)phenyl-β-D-xylopyranoside
Para(aluminiumoxycarbonyl)phenyl 1-thio-β-D-xylopyranoside
C-Para(aluminiumoxycarbonyl)benzyl-β-D-xylopyranoside [aluminium 4-(C-β-D-xylopyranosyl)methyl-1-benzoate]
N-Paracarbamoylphenyl-D-xylopyranosylamine
n-Nonyl 1-thio-β-D-xylopyranoside
n-Decyl 1-thio-β-D-xylopyranoside
n-Undecyl 1-thio-β-D-xylopyranoside
n-Lauryl 1-thio-β-D-xylopyranoside
n-Tridecyl 1-thio-β-D-xylopyranoside
n-Myristyl 1-thio-β-D-xylopyranoside
n-Pentadecyl 1-thio-β-D-xylopyranoside
n-Cetyl 1-thio-β-D-xylopyranoside
n-Heptadecyl 1-thio-β-D-xylopyranoside
n-Stearyl 1-thio-β-D-xylopyranoside
n-Eicosyl 1-thio-β-D-xylopyranoside
n-Docosyl 1-thio-β-D-xylopyranoside
n-Tetracosyl 1-thio-β-D-xylopyranoside
Isopropyl 1-thio-β-D-xylopyranoside
Isobutyl 1-thio-β-D-xylopyranoside
sec-Butyl 1-thio-β-D-xylopyranoside
Isoamyl 1-thio-β-D-xylopyranoside
Neopentyl 1-thio-β-D-xylopyranoside
sec-Isoamyl 1-thio-β-D-xylopyranoside
Isohexyl 1-thio-β-D-xylopyranoside
Isononyl 1-thio-β-D-xylopyranoside
Isolauryl 1-thio-β-D-xylopyranoside
Isopentadecyl 1-thio-β-D-xylopyranoside
Isostearyl 1-thio-β-D-xylopyranoside
Allyl 1-thio-β-D-xylopyranoside
Propargyl 1-thio-β-D-xylopyranoside
C-n-Hexyl-β-D-xylopyranoside (C-β-D-Xylopyranosylhexane)
C-n-Heptyl-β-D-xylopyranoside (C-β-D-Xylopyranosylheptane)
C-n-Octyl-β-D-xylopyranoside (C-β-D-Xylopyranosyloctane)
C-n-Nonyl-β-D-xylopyranoside (C-β-D-Xylopyranosylnonane)
C-n-Decyl-β-D-xylopyranoside (C-β-D-Xylopyranosyldecane)
C-n-Undecyl-β-D-xylopyranoside (C-β-D-Xylopyranosylundecane)
C-n-Lauryl-β-D-xylopyranoside (C-β-D-Xylopyranosyldodecane)
C-n-Tridecyl-β-D-xylopyranoside (C-β-D-Xylopyranosyltridecane)
C-n-Myristyl-β-D-xylopyranoside (C-β-D-Xylopyranosyltetradecane)
C-n-Pentadecyl-β-D-xylopyranoside (C-β-D-Xylopyranosylpentadecane)
C-n-Cetyl-β-D-xylopyranoside (C-β-D-Xylopyranosylhexadecane)
C-n-Heptadecyl-β-D-xylopyranoside (C-β-D-Xylopyranosylheptadecane)
C-n-Stearyl-β-D-xylopyranoside (C-β-D-Xylopyranosyloctadecane)
C-n-Nonadecyl-β-D-xylopyranoside (C-β-D-Xylopyranosylnondecane)
C-n-Eicosyl-β-D-xylopyranoside (C-β-D-Xylopyranosyleicosane)
C-n-Henicosyl-β-D-xylopyranoside (C-β-D-Xylopyranosylhenicosane)
C-n-Docosyl-β-D-xylopyranoside (C-β-D-Xylopyranosyldocosane)
C-n-Tricosyl-β-D-xylopyranoside (C-β-D-Xylopyranosyltricosane)
C-n-Tetracosyl-β-D-xylopyranoside (C-β-D-Xylopyranosyltetracosane)
C-n-Pentacosyl-β-D-xylopyranoside (C-β-D-Xylopyranosylpentacosane)

5. A method of reducing the quantity of proteoglycan in cell membranes comprising treating said cell membranes with an effective amount of the compound of claim 1.

6. A method of inhibiting the effect of platelet agglutinating agents in the blood of a warm blooded animal containing the same comprising administering to said warm blooded animal an effective amount of the compound of claim 1.

* * * * *